(12) United States Patent
Nishizaki et al.

(10) Patent No.: US 9,512,152 B2
(45) Date of Patent: Dec. 6, 2016

(54) PHOSPHOLIPID COMPOUND CONTAINING UNSATURATED FATTY ACID DERIVATIVE HAVING CYCLOPROPANE RING

(71) Applicant: NISHIZAKI BIOINFORMATION RESEARCH INSTITUTE, Kobe-shi, Hyogo (JP)

(72) Inventors: Tomoyuki Nishizaki, Kobe (JP); Akito Tanaka, Toyonaka (JP)

(73) Assignee: Nishizaki Bioinformation Research Institute, Kobe (JP)

( * ) Notice: Subject to any disclaimer, the term of this patent is extended or adjusted under 35 U.S.C. 154(b) by 0 days.

(21) Appl. No.: 14/767,532

(22) PCT Filed: Feb. 14, 2014

(86) PCT No.: PCT/JP2014/053448
§ 371 (c)(1),
(2) Date: Aug. 12, 2015

(87) PCT Pub. No.: WO2014/126191
PCT Pub. Date: Aug. 21, 2014

(65) Prior Publication Data
US 2015/0376213 A1 Dec. 31, 2015

(30) Foreign Application Priority Data
Feb. 15, 2013 (JP) .................. 2013-027992

(51) Int. Cl.
*C07F 9/06* (2006.01)
*A61K 31/683* (2006.01)
(Continued)

(52) U.S. Cl.
CPC ............ *C07F 9/062* (2013.01); *A61K 31/661* (2013.01); *A61K 31/683* (2013.01);
(Continued)

(58) Field of Classification Search
CPC ...... C07F 9/062; A61K 31/661; A61K 31/683
See application file for complete search history.

(56) References Cited

U.S. PATENT DOCUMENTS

| 7,468,389 B2 | 12/2008 | Nishizaki et al. |
| 9,163,032 B2 | 10/2015 | Alkon et al. |

(Continued)

FOREIGN PATENT DOCUMENTS

| EP | 3006033 A1 | 4/2016 |
| JP | 2005-247728 A | 9/2005 |

(Continued)

OTHER PUBLICATIONS

Turner, D.L., et al., The snthesis of phosphatidylethanolamind and Phosphaticylserine containing acetylenic or cyclopropane fatty acids and the activity of these phosphatides in blood coagulation,1970, Lipids, vol. 5, No. 7, pp. 650-657.*

(Continued)

*Primary Examiner* — Yate K Cutliff
(74) *Attorney, Agent, or Firm* — Leydig, Voit & Mayer, Ltd.

(57) ABSTRACT

The invention provides a phospholipid compound containing unsaturated fatty acid having a cyclopropane ring such as 8-[2-(2-pentyl-cyclopropylmethyl)-cyclopropyl]-octanoic acid (DCP-LA) and 8-(2-octylcyclopropyl)octanoic acid (DCP-OA) and the like, particularly 1,2-o-bis-[8-{2-(2-pentyl-cyclopropylmethyl)-cyclopropyl}-octanoyl]-sn-glycero-3-phosphatidylethanolamine (diDCP-LA-PE), which has a cognitive function improving effect and an anti-diabetes action, and which is useful as a medicine such as a therapeutic drug for dementia, a therapeutic drug for diabetes and the like.

12 Claims, 12 Drawing Sheets

(51) Int. Cl.
  A61K 31/685 (2006.01)
  C07F 9/117 (2006.01)
  C07F 9/10 (2006.01)
  A61K 31/661 (2006.01)
(52) U.S. Cl.
  CPC ............ *A61K 31/685* (2013.01); *C07F 9/106* (2013.01); *C07F 9/117* (2013.01)

(56) References Cited

U.S. PATENT DOCUMENTS

| | | | |
|---|---|---|---|
| 2005/0075393 A1 | 4/2005 | Nishizaki et al. | |
| 2010/0022645 A1 | 1/2010 | Nelson et al. | |
| 2012/0149768 A1 | 6/2012 | Nelson et al. | |
| 2014/0323456 A1 | 10/2014 | Alkon et al. | |

FOREIGN PATENT DOCUMENTS

| | | |
|---|---|---|
| JP | 2009-007329 A | 1/2009 |
| JP | 2011-529503 A | 12/2011 |
| WO | WO 02/50013 A1 | 6/2002 |
| WO | WO 2013/071281 A1 | 5/2013 |

OTHER PUBLICATIONS

Zhu, C. et al., Syntehsis of a novel lysophosphatidylcholine, 2001, J. Nat. Prod., 64(1), pp. 98-99.*

Nagai, K., et al., Dilinoleoyl-phosphatidylethanolamine from Hericium erinaceum protects against ER stress-dependent Neuro2a cell death via protein kinase C pathway, 2006, Journal of Nutritional Biochemistry, vol. 17, pp. 525-530.*

Kanno et al., "The linoleic acid derivative DCP-LA selectively activates PKC-$\epsilon$, possibly binding to the phosphatidylserine binding site," *Journal of Lipid Research*, 47: 1146-1156 (2006).

Nagai et al., "Dilinoleoyl-phosphatidylethanolamine from *Hericium erinaceum* protects against ER stress-dependent Neuro2a cell death via protein kinase C pathway," *Journal of Nutritional Biochemistry*, 17: 525-530 (2006).

Turner et al., "The Synthesis of Phosphatidylethanolamine and Phosphatidylserine Containing Acetylenic or Cyclopropane Fatty Acids and the Activity of These Phosphatides in Blood Coagulation," *Lipids*, 5(7): 650-657 (1970).

Yaguchi et al., "1-Palmitoyl-2-oleoyl-*sn*-glycero-3-phosphocholine improves cognitive decline by enhancing long-term depression," *Behavioural Brain Research*, 204: 129-132 (2009).

Yaguchi et al., "Dilinoleoylphosphatidylcholine ameliorates scopolamine-induced impairment of spatial learning and memory by targeting $\alpha$7 nicotinic ACh receptors," *Life Sciences*, 84: 263-266 (2009).

Zhu et al., "Synthesis of a Novel Lysophosphatidylcholine," *Journal of Natural Products*, 64(1): 98-99 (2001).

Chemical Abstracts Service, "Protective effects of dilinoleoylphosphatidylethanolamine on endoplasmic reticurum stress induced neuronal and pancreatic beta-cell death," Chemical Abstracts Database Accession No. 2010:206691 (2010) [abstract of Kaoru et al., Daizu Tanpakushitsu Kenkyu, 12: 153-157 (2009)].

Kanno et al., "Effects of Newly Synthesized DCP-LA-Phospholipids on Protein Kinase C and Protein Phosphatases," *Cellular Physiology and Biochemistry*, 31(4-5): 555-564 (2013).

Kanno et al., "8-[2-(2-Pentyl-Cyclopropylmethyl)-Cyclopropyl]-Octanoic Acid and Its Diastereomers Improve Age-Related Cognitive Deterioration," *Lipids*, 47(7): 687-695 (2012).

Mukai et al., "Inhibition of Tumor Invasion and Metastasis by a Novel Lysophosphatidic Acid (Cyclic LPA)," *International Journal of Cancer*, 81(6): 918-922 (1999).

Perly et al., "Effects of the Replacement of a Double Bond by a Cyclopropane Ring in Phosphatidylethanolamines: A $^2$H NMR Study of Phase Transitions and Molecular Organization," *Biochemistry*, 24(4): 1055-1063 (1985).

Silvius et al., "Effects of Phospholipid Acyl Chain Structure on Thermotropic Phase Properties. 2: Phosphatidylcholines With Unsaturated or Cyclopropane Acyl Chains," *Chemistry and Physics of Lipids*, 25(2): 125-134 (1979).

Tsuchiya et al., "DCP-LA-Phosphatidylinositol and Its Enantiomer Exhibit Different Bioactivities," *Cellular Physiology and Biochemistry*, 33(2): 300-309 (2014).

European Patent Office, Supplementary European Search Report in European Patent Application No. 14751672 (Jun. 7, 2016).

* cited by examiner

PHOSPHOLIPID COMPOUND CONTAINING UNSATURATED FATTY ACID DERIVATIVE HAVING CYCLOPROPANE RING

CROSS-REFERENCE TO RELATED APPLICATIONS

This patent application is the U.S. national phase of International Patent Application No. PCT/JP2014/053448, filed Feb. 14, 2014, which claims the benefit of Japanease Patent Application No. 2013-027992, filed on Feb. 15, 2013, which are incorporated by reference in their entireties herein.

TECHNICAL FIELD

The present invention relates to a phospholipid compound having a cognitive function improving effect and/or a diabetes treatment effect. More particularly, it relates to a phospholipid compound containing an unsaturated fatty acid derivative having a cyclopropane ring.

BACKGROUND ART

In recent years, dementia has become a significant medical problem worldwide. Dementia is a disease associated with various symptoms mainly including learning and memory disorders and impaired judgment, in which the symptoms and progression thereof vary depending on the causative diseases thereof. In any case, they are common in that they markedly impair the quality of life of the patients. In consideration of the fact that dementia forces huge labor to the caregivers including patients' families, it is a very serious social problem. It is predicted that the dementia patients will further increase hereafter in Japan, since an increase in the population of elderly people due to prolongation of life span is related to an increase in the dementia patients. In addition, there are many people suffering from cognitive impairment due to aging, which is not classified as dementia.

Various compounds capable of improving dementia have been reported. 8-[2-(2-Pentyl-cyclopropylmethyl)-cyclopropyl]-octanoic acid (DCP-LA), which is a linoleic acid derivative, is a compound having a long-term enhancing action on synapse transmission efficiency, which can delay metabolism in the body and can maintain stable LTP (long-teLm potentiation)-like enhancement of synapse transmission (patent document 1). LTP is considered to be involved in the onset of, for example, various neurological and mental diseases such as Alzheimer's disease and the like, and therefore, a substance that induces LTP expression has a possibility of providing a therapeutic or prophylactic drug for these neurological and mental diseases including dementia.

On the other hand, phospholipid has also been reported to be effective for the improvement of cognitive function and for neurodegenerative diseases. For example, 1,2-dilinoleoyl-sn-glycero-3-phosphocholine and 1-palmitoyl-2-oleoyl-sn-glycero-3-phosphocholine have been reported to improve spatial learning disorder and memory disorder induced by scopolamine, or mild cognitive impairment and dementia (non-patent documents 1, 2).

Also, phosphatidylethanolamine is a phospholipid, which is one of the main components of biological membrane, and is being marketed along with phosphatidylserine and the like as health foods. Of phosphatidylethanolamines, particularly, dilinoleoyl•phosphatidylethanolamine (containing two linoleic acids as fatty acids) has been reported to have cell death induction suppressive activity, particularly, endoplasmic reticulum stress suppressive activity and, due to such activity, dilinoleoyl•phosphatidylethanolamine can be used for pharmaceutical application, particularly for the prophylaxis and/or treatment of neurodegenerative disease (patent document 2).

However, it is not known that a compound wherein an unsaturated fatty acid derivative having a cyclopropane ring such as DCP-LA and the like and phospholipid are bonded is effective for the improvement of cognitive function, and there is no report on the pharmacological effect provided by such compound.

DOCUMENT LIST

Patent Documents patent document 1: WO 02/50013
patent document 2: JP-A-2005-247728

Non-Patent Documents non-patent document 1: Yaguchi T, Nagata T, Nishizaki T. Dilinoleoylphosphatidylcholine ameliorates scopolamine-induced impairment of spatial learning and memory by targeting alpha-7 nicotinic ACh receptors. Life Sci 2009; 84: 263-6 non-patent document 2: Yaguchi T, Nagata T, Nishizaki T. 1-Palmitoyl-2-oleoyl-sn-glycero-3-phosphocholine improves cognitive decline by enhancing long-term depression. Behav Brain Res 2009; 204: 129-32

SUMMARY OF THE INVENTION

Problems to be Solved by the Invention

The present invention aims to provide a phospholipid compound containing an unsaturated fatty acid derivative having a cyclopropane ring, particularly a phospholipid compound having a cognitive function improving effect and/or a diabetes treatment effect, and pharmaceutical use of the compound.

Means of Solving the Problems

The present inventors have further conducted intensive studies in an attempt to obtain a medicine capable of more effectively improving the cognitive function. As a result, they have found that a phospholipid compound containing an unsaturated fatty acid derivative having a cyclopropane ring has various superior pharmacological actions useful for the improvement of cognitive function, and further confirmed that the compound also has a pharmacological action useful for the treatment of diabetes, which resulted in the completion of the present invention. Accordingly, the present invention is as described below.

[1] A medicine comprising a phospholipid compound containing an unsaturated fatty acid having a cyclopropane ring as an active ingredient.

[2] The medicine of the above-mentioned [1], wherein the unsaturated fatty acid having a cyclopropane ring is an unsaturated fatty acid having a double bond converted to a cyclopropane ring.

[3] The medicine of the above-mentioned [1], wherein the unsaturated fatty acid having a cyclopropane ring is 8-[2-(2-pentyl-cyclopropylmethyl)-cyclopropyl]-octanoic acid (DCP-LA) or 8-(2-octylcyclopropyl)octanoic acid (DCP-OA).

[4] The medicine of the above-mentioned [1], wherein the phospholipid compound is phosphatidylethanolamine (PE), phosphatidylserine (PS), phosphatidylcholine (PC), or phosphatidylinositol (PI).

[5] The medicine of the above-mentioned [1], wherein the phospholipid compound is 1,2-o-bis-[8-{2-(2-pentyl-cyclopropylmethyl)-cyclopropyl}-octanoyl]-sn-glycero-3-phosphatidylethanolamine (diDCP-LA-PE), 1,2-o-bis-[8-{2-(2-pentyl-cyclopropylmethyl)-cyclopropyl}-octanoyl]-sn-glycero-3-phosphatidyl-L-serine (diDCP-LA-PS), 1,2-o-bis-[8-{2-(2-pentyl-cyclopropylmethyl)-cyclopropyl}-octanoyl]-sn-3-glycero-3-phosphatidylcholine (diDCP-LA-PC), 1,2-o-bis-[8-{2-(2-pentyl-cyclopropylmethyl)-cyclopropyl}-octanoyl]-sn-glycero-3-phosphatidyl-D-1-inositol(diDCP-LA-PI), or 1,2-o-bis-[8-{2-(2-pentyl-cyclopropylmethyl)-cyclopropyl}-octanoyl]-sn-glycero-3-phosphatidyl-L-1-inositol (diDCP-LA-PI ent).

[6] The medicine of any of the above-mentioned [1]-[5], which is a therapeutic drug for diabetes.

[7] The medicine of the above-mentioned [6], wherein the diabetes are type 1 diabetes.

[8] The medicine of the above-mentioned [6], wherein the diabetes is type 2 diabetes.

[9] The medicine of the above-mentioned [6], wherein the diabetes includes type 1 and type 2 diabetes.

[10] The medicine of any of the above-mentioned [1]-[5], which is a therapeutic drug for dementia.

[11] The medicine of the above-mentioned [10], wherein the dementia is Alzheimer-type dementia.

[12] The medicine of any of the above-mentioned [1]-[5], which is an anti-aging drug.

[13] A reagent comprising a phospholipid compound containing an unsaturated fatty acid derivative having a cyclopropane ring as an active ingredient.

[14] The reagent of the above-mentioned [13], wherein the unsaturated fatty acid having a cyclopropane ring is an unsaturated fatty acid converted a double bond to a cyclopropane ring.

[15] The reagent of the above-mentioned [13], wherein the unsaturated fatty acid having a cyclopropane ring is 8-[2-(2-pentyl-cyclopropylmethyl)-cyclopropyl]-octanoic acid (DCP-LA) or 8-(2-octylcyclopropyl)octanoic acid (DCP-OA).

[16] The reagent of the above-mentioned [13], wherein the phospholipid compound is phosphatidylethanolamine (PE), phosphatidylserine (PS), phosphatidylcholine (PC), or phosphatidylinositol (PI).

[17] The reagent of the above-mentioned [13], wherein the phospholipid compound is 1,2-o-bis-[8-{2-(2-pentyl-cyclopropylmethyl)-cyclopropyl}-octanoyl]-sn-glycero-3-phosphatidylethanolamine (diDCP-LA-PE), 1,2-o-bis-[8-{2-(2-pentyl-cyclopropylmethyl)-cyclopropyl}-octanoyl]-sn-glycero-3-phosphatidyl-L-serine (diDCP-LA-PS), 1,2-o-bis-[8-{2-(2-pentyl-cyclopropylmethyl)-cyclopropyl}-octanoyl]-sn-3-glycero-3-phosphatidylcholine (diDCP-LA-PC), 1,2-o-bis-[8-{2-(2-pentyl-cyclopropylmethyl)-cyclopropyl}-octanoyl]-sn-glycero-3-phosphatidyl-D-1-inositol(diDCP-LA-PI), or 1,2-o-bis-[8-{2-(2-pentyl-cyclopropylmethyl)-cyclopropyl}-octanoyl]-sn-glycero-3-phosphatidyl-L-1-inositol (diDCP-LA-PI ent).

[18] The reagent of any of the above-mentioned [13]-[17], which is a protein tyrosine phosphatase 1B inhibitor.

[19] The reagent of any of the above-mentioned [13]-[17], which is an Akt activator.

[20] The reagent of any of the above-mentioned [13]-[17], which is a protein phosphorylated enzyme C (PKC) activator.

[21] The reagent of the above-mentioned [20], wherein the PKC is PKCι and/or PKCζ.

[22] A compound selected from the group consisting of 1,2-o-bis-[8-{2-(2-pentyl-cyclopropylmethyl)-cyclopropyl}-octanoyl]-sn-glycero-3-phosphatidylethanolamine (diDCP-LA-PE), 1,2-o-bis-[8-{2-(2-pentyl-cyclopropylmethyl)-cyclopropyl}-octanoyl]-sn-glycero-3-phosphatidyl-L-serine (diDCP-LA-PS), 1,2-o-bis-[8-{2-(2-pentyl-cyclopropylmethyl)-cyclopropyl}-octanoyl]-sn-3-glycero-3-phosphatidylcholine (diDCP-LA-PC), 1,2-o-bis-[8-{2-(2-pentyl-cyclopropylmethyl)-cyclopropyl}-octanoyl]-sn-glycero-3-phosphatidyl-D-1-inositol (diDCP-LA-PI), and 1,2-o-bis-[8-{2-(2-pentyl-cyclopropylmethyl)-cyclopropyl}-octanoyl]-sn-glycero-3-phosphatidyl-L-1-inositol (diDCP-LA-PI ent).

[23] A method for the prophylaxis or treatment of diabetes, comprising administering an effective amount of a phospholipid compound containing an unsaturated fatty acid having a cyclopropane ring to a patient in need thereof.

[24] The method of the above-mentioned [23], wherein the phospholipid compound is diDCP-LA-PE, diDCP-LA-PS, diDCP-LA-PC, diDCP-LA-PI, or diDCP-LA-PI ent.

[25] A method for the prophylaxis or treatment of dementia, comprising administering an effective amount of a phospholipid compound containing an unsaturated fatty acid having a cyclopropane ring to a patient in need thereof.

[26] The method of the above-mentioned [25], wherein the phospholipid compound is diDCP-LA-PE, diDCP-LA-PS, diDCP-LA-PC, diDCP-LA-PI, or diDCP-LA-PI ent.

[27] A phospholipid compound containing an unsaturated fatty acid having a cyclopropane ring for the prophylaxis or treatment of diabetes.

[28] The phospholipid compound of the above-mentioned [27], which is diDCP-LA-PE, diDCP-LA-PS, diDCP-LA-PC, diDCP-LA-PI, or diDCP-LA-PI ent.

[29] A phospholipid compound containing an unsaturated fatty acid having a cyclopropane ring for the prophylaxis or treatment of dementia.

[30] The phospholipid compound of the above-mentioned [29], which is diDCP-LA-PE, diDCP-LA-PS, diDCP-LA-PC, diDCP-LA-PI, or diDCP-LA-PI ent.

Effect of the Invention

A phospholipid compound containing an unsaturated fatty acid having a cyclopropane ring, which is provided by the present invention, has pharmacological actions (protein tyrosine phosphatase 1B (PTP1B) inhibitory action, Akt activating action, protein phosphorylated enzyme C (PKC) activating action, PKCι and PKCζ activating action, promoting action on transfer of glucose transporter 4 (GLUT4) to cellular membrane and non-insulin-dependent blood glucose level lowering action) superior in the improvement of cognitive function and/or treatment of diabetes, and therefore, is useful as a therapeutic drug for dementia or a therapeutic drug for diabetes. It is also useful as various reagents based on such pharmacological actions.

DESCRIPTION OF EMBODIMENTS

Figure 1:
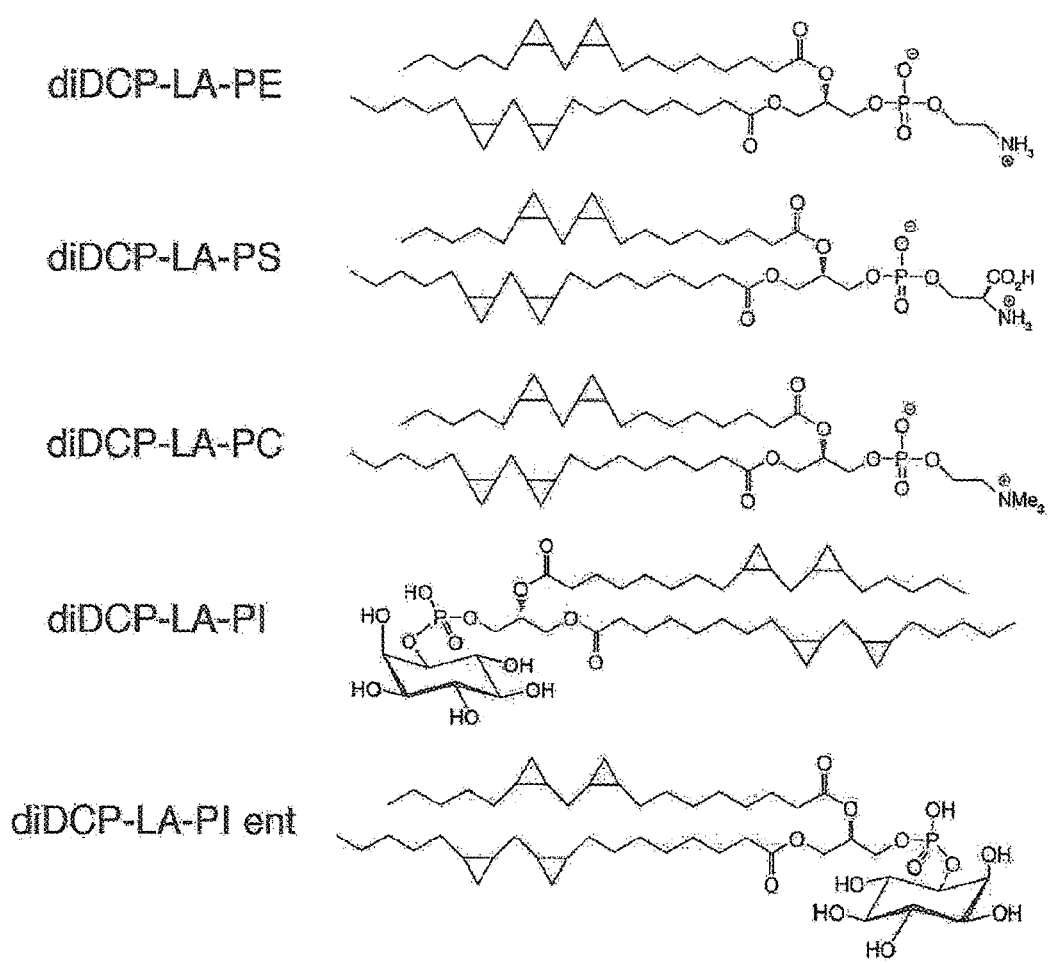
FIG. 1 shows the structure of the phospholipid compound of the present invention.

The present invention is explained in detail in the following.

The present invention provides a medicine containing a phospholipid compound containing an unsaturated fatty acid having a cyclopropane ring as an active ingredient. For convenience, the phospholipid compound is hereinafter also referred to as the phospholipid compound of the present invention, and the medicine is also referred to as the medicine of the present invention. The medicine is a concept including a therapeutic drug for dementia, a therapeutic drug for diabetes, an anti-aging drug and the like as mentioned below.

The "unsaturated fatty acid having a cyclopropane ring" is an unsaturated fatty acid wherein a double bond is converted to a cyclopropane ring, and the number of the conversion is 1 or more, preferably 1 or 2, more preferably 2, depending on the number of the original double bond. The unsaturated fatty acid is not particularly limited as long as it is a fatty acid having at least one double bond in a molecule, and may be any of a monovalent unsaturated fatty acid, a polyvalent unsaturated fatty acid, a cis-type unsaturated fatty acid, or a trans-type unsaturated fatty acid.

Examples of the monovalent unsaturated fatty acid include oleic acid, pulmitoleic acid, petroselinic acid, erucic acid, brassidic acid, obtusilic acid, kapurein acid, undecylenoic acid, linder acid, tudu acid, fiseterinic acid, myristoleic acid, pulmitoleic acid, elaidic acid, asclepinic acid, vaccenic acid, gadoleic acid, gondoic acid, cetoleic acid, cis-6-hexadecene acid and the like.

Examples of the polyvalent unsaturated fatty acid include linoleic acid, linolenic acid, γ-linolenic acid, ricinoleic acid, α-eleostearic acid, β-eleostearic acid, punicic acid, trans-10-octadecadienoic acid, trans-12-octadecadienoic acid and the like.

Preferred are linoleic acid (cis,cis-9,12-octadienoic acid) and oleic acid (cis-9-octadecenoic acid), more preferably linoleic acid.

In the case of a polyvalent unsaturated fatty acid, all double bonds may be converted to cyclopropane rings, and a part of the double bond may be converted to a cyclopropane ring.

Preferred as the "unsaturated fatty acid having a cyclopropane ring" in the present invention are 8-[2-(2-pentyl-cyclopropylmethyl)-cyclopropyl]-octanoic acid (DCP-LA) wherein the double bond of linoleic acid is converted to a cyclopropane ring; and 8-(2-octylcyclopropyl)octanoic acid (DCP-OA) wherein the double bond of oleic acid is converted to a cyclopropane ring. More preferred is DCP-LA.

Phospholipid is largely divided into two: glycerophospholipid having glycerol as the skeleton, and sphingophospholipid having sphingosine as the skeleton. It has a structure wherein glycerol and sphingosine are the central skeletons, fatty acid and phosphoric acid are bonded thereto, and alcohol is ester-bonded to phosphoric acid. While the phospholipid compound of the present invention may be any of glycerophospholipid and sphingophospholipid, it is preferably glycerophospholipid. A molecule wherein fatty acid is ester bonded to the C1 and C2-positions of glycerol, and phosphoric acid is ester bonded to the C3-position is called phosphatidic acid and, in one preferable embodiment of the present invention, the fatty acid at the C1 and C2-positions is the above-mentioned "unsaturated fatty acid having a cyclopropane ring". Two unsaturated fatty acids may be the same or different, and preferably the same. Examples of alcohol ester-bonded to phosphoric acid include choline, ethanolamine, inositol, serine and the like. Preferred is ethanolamine.

It should be noted that the phospholipid compound of the present invention may contain one or more stereoisomers (e.g., optical isomer, geometric isomer) due to an asymmetric carbon atom or a double bond, and all of such isomers and mixtures thereof are encompassed within the scope of the present invention.

The phospholipid compound of the present invention can be synthesized according to a general synthesis method of phospholipid (e.g., the method described in "The Chemical Society of Japan ed., 5th ed., Jikken Kagaku Kouza 16, synthesis of organic compound (kyo); carboxylic acid•amino acid•peptide, chapter 3, phosphate"), except that the fatty acid to be contained is an unsaturated fatty acid having a cyclopropane ring. More particularly, the compound can be synthesized according to the method described in Examples.

An unsaturated fatty acid having a cyclopropane ring can be produced by, for example, the method shown in patent document 1 or a method analogous thereto. In addition, it may be extracted from a naturally occurring substance. The production method of DCP-LA is described in patent document 1.

Preferred as the "phospholipid compound containing an unsaturated fatty acid having a cyclopropane ring" are 1,2-o-bis-[8-{2-(2-pentyl-cyclopropylmethyl)-cyclopropyl}-octanoyl]-sn-glycero-3-phosphatidylethanolamine (diDCP-LA-PE), 1,2-o-bis-[8-{2-(2-pentyl-cyclopropylmethyl)-cyclopropyl}-octanoyl]-sn-glycero-3-phosphatidyl-L-serine (diDCP-LA-PS), 1,2-o-bis-[8-{2-(2-pentyl-cyclopropylmethyl)-cyclopropyl}-octanoyl]-sn-3-glycero-3-phosphatidylcholine (diDCP-LA-PC), 1,2-o-bis-[8-{2-(2-pentyl-cyclopropylmethyl)-cyclopropyl}-octanoyl]-sn-glycero-3-phosphatidyl-D-1-inositol (diDCP-LA-PI), and 1,2-o-bis-[8-{2-(2-pentyl-cyclopropylmethyl)-cyclopropyl}-octanoyl]-sn-glycero-3-phosphatidyl-L-1-inositol (diDCP-LA-PI ent), more preferred is diDCP-LA-PE.

The diDCP-LA-PI ent is a nonnatural type optical isomer of diDCP-LA-PI.

The structure of each phospholipid compound is shown in FIG. 1.

The phospholipid compound of the present invention may also be used in the form of a salt thereof. Such salt is not particularly limited, and a salt acceptable as a medicine or food is preferable. Examples thereof include salts with inorganic base (e.g., alkali metal such as sodium, potassium and the like; alkaline earth metal such as calcium, magnesium and the like; aluminum, ammonium), organic base (e.g., trimethylamine, triethylamine, pyridine, picoline, ethanolamine, diethanolamine, triethanolamine, dicyclohexylamine, N,N-dibenzylethylenediamine), inorganic acid (e.g., hydrochloric acid, hydrobromic acid, nitric acid, sulfuric acid, phosphoric acid), organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acid (e.g., arginine, lysine, ornithine) or acidic amino acid (e.g., aspartic acid, glutamic acid) and the like.

The phospholipid compound of the present invention has (1) protein tyrosine phosphatase 1B (PTP1B) inhibitory action, (2) Akt activating action, (3) protein phosphorylated enzyme C (PKC) activating action, (4) PKCι and PKCζ activating action, (5) promoting action on transfer of glucose transporter 4 (GLUT4) to cellular membrane, and (6) insulin non-dependent blood glucose level-decreasing action, as shown by the data in the Examples. Having these superior pharmacological actions, the phospholipid compound of the present invention is particularly useful for the prophylaxis or treatment of diseases associated with cognitive impairment, and the prophylaxis or treatment of diabetes, and is provided as a pharmaceutical product.

Examples of the disease or condition associated with cognitive impairment include, specifically, various diseases and condition including dementia (e.g., senile dementia, dementia caused by various diseases such as Alzheimer-type dementia (Alzheimer's disease), cerebrovascular dementia, posttraumaic dementia, dementia caused by brain tumor, dementia caused by chronic subdural hematoma, dementia caused by normal pressure brain hydrocephalus, postmeningitis dementia, Parkinson type dementia and the like), cognitive impairment no dementia (e.g., mild cognitive impairment (MCI)), learning or memory disorders (e.g., learning and memory disorders associated with developmental brain disorder) and the like. As used in the present specification, "prophylaxis" means prevention of exteriorization of cognitive impairment, learning•memory disorder and the like in test subjects free from such symptoms, and the "treatment" means mitigation, prevention of exacerbation or delay of cognitive impairment, learning•memory disorder and the like in test subjects showing such symptoms. The "improvement" in test subjects free from cognitive impairment, learning•memory disorder and the like means improvement of cognitive ability, and learning•memorizing ability, and that in test subjects showing cognitive impairment, learning•memory disorder and the like means mitigation of the symptoms, preferably mitigation of the symptoms to the level posing no difficulty in daily living.

Preferable examples of the applicable disease include Alzheimer's disease. In view of the above-mentioned properties, an effect as an anti-aging drug can also be expected.

Diabetes is a disease caused by disordered metabolism mechanism of sugar due to insufficient insulin action, and is divided into two: insulin dependent diabetes (IDDM or type 1 diabetes) and non-insulin dependent diabetes (NIDDM or type 2 diabetes). The former is a type in which insulin is not secreted or secretion amount is extremely small even when the blood glucose level increased by food ingestion, and the latter is a type in which the response mechanism of peripheral tissue does not operate normally and the blood glucose level does not fall, even though insulin is normally secreted.

The present invention is useful for the both types of diabetes.

Examples of the pharmacological action of the phospholipid compound of the present invention include the following.

(1) PTP1B Inhibitory Action

Protein tyrosine phosphatase (PTP) 1B is a cytosolic tyrosine phosphatase that controls phosphorylation state of tyrosine kinase, thereby involved in the adjustment of tyrosine kinase. PTP1B is considered one of the attenuation factors of insulin signal transduction, and inhibition of this enzyme is considered to be useful for the treatment of diabetes. Moreover, as the involvement of protein phosphorylation in the neural activity attracts attention in recent years, application of PTP1B inhibition to neurodegenerative diseases has been expected.

Examples of reports indicating the possibility of a PTP1B inhibitor for application to pharmaceutical use include the following.
1. Sun T, Wang Q, Yu Z, Zhang Y, Guo Y, Chen K, Shen X, Jiang H. Hyrtiosal, a PTP1B inhibitor from the marine sponge Hyrtios erectus, shows extensive cellular effects on PI3K/AKT activation, glucose transport, and TGFb/Smad2 signaling. Chembiochem 2007; 8 (2): 187-193.
2. Lin Z, Zhang Y, Zhang Y, Shen H, Hu L, Jiang H, Shen X. Oleanolic acid derivative NPLC441 potently stimulates glucose transport in 3T3-L1 adipocytes via a multi-target mechanism. Biochem Pharmacol 2008; 76 (10): 1251-1262.
3. Zhang Y, Zhang H, Yao XG, Shen H, Chen J, Li C, Chen L, Zheng M, Ye J, Hu L, Shen X, Jiang H. (+)-Rutamarin as a dual inducer of both GLUT4 translocation and expression efficiently ameliorates glucose homeostasis in insulin-resistant mice. PLoS One 2012; 7 (2): e31811.

(2) Akt Activating Action

It is one kind of Akt (also to be referred to as protein kinase B) serine threonine phosphorylated enzyme, and activation thereof is considered to essentially require phosphorylation of two amino acids of threonine 308 group (Thr 308) and serine 473 group (Ser 473). Akt has a function to specifically phosphorylate intracellular protein serine or threonine residue, and is known as an anti-aging factor. Akt plays the most important action in the insulin/insulin receptor signal pathway relating to the promotion of transfer of glucose transporter 4 (GLUT4) into cellular membrane/intracellular uptake of glucose. Therefore, an Akt activator can be an effective therapeutic drug for diabetes.

Examples of reports showing the possibility of Akt activator for application to pharmaceutical use include the following.
1. Maarbjerg S J, Sylow L, Richter E A. Current understanding of increased insulin sensitivity after exercise-emerging candidates. Acta Physiol 2011; 202: 323-335.
2. Bryant N J, Govers R, James D E: Regulated transport of the glucose transporter GLUT4. Nat Rev Mol Cell Biol 2002; 3: 267-277.

(3) Protein Phosphorylated Enzyme C (PKC) Activating Action

PKC was identified as one of the maximum gene family of non-receptor serine-threonine protein kinase (Kikkawa et al., J. Biol. Chem., 257, 13341 (1982)). Many physiological signaling mechanisms are considered to be caused by this enzyme. The PKC gene family is currently constituted of 11 genes classified into 4 subgrounds: 1) classical PKC$\alpha$, $\beta_1$, $\beta_2$ and $\gamma$, 2) novel PKC$\delta$, $\epsilon$, $\eta$ and $\theta$, 3) atypical PKC$\zeta$, $\lambda$, $\eta$ and $\iota$, and 4) PKC$\mu$. PKC$\epsilon$ enhances synaptic activity by using $\alpha$7 acetylcholine receptor expressed in the presynaptic terminal as a target, and shows a cognitive function improving effect (documents 1-4 below). PKC$\zeta$ and $\iota$ have an action to promote transition of GLUT4 into the cellular membrane as a downstream signal of insulin/insulin receptor (Bryant N J et al., Nat Rev Mol Cell Biol 2002; 3: 267-277; document 5 below).

Examples of reports showing the possibility of PKC activator for application to pharmaceutical use include the following.
1. Yamamoto S, Kanno T, Nagata T, Yaguchi T, Tanaka A, Nishizaki T. The linoleic acid derivative FR236924 facilitates hippocampal synaptic transmission by enhancing activity of presynaptic a7 acetylcholine receptors on the glutamatergic terminals. Neuroscience 2005; 130 (1): 207-213.
2. Yaguchi T, Nagata T, Mukasa T, Fujikawa H, Yamamoto H, Yamamoto S, Iso H, Tanaka A, Nishizaki T. Linoleic acid derivative DCP-LA improves learning impairment in SAMP8. Neuroreport 2006; 17 (1): 105-108.
3. Shimizu T, Kanno T, Tanaka A, Nishizaki T. $\alpha$,$\beta$-DCP-LA selectively activates PKC-$\epsilon$ and stimulates neurotransmitter release with the highest potency among 4 diastereomers. Cell Physiol Biochem 2011; 27 (2): 149-158.
4. Kanno T, Yaguchi T, Shimizu T, Tanaka A, Nishizaki T. 8-[2-(2-Pentyl-cyclopropylmethyl)-cyclopropyl]-octanoic acid and its diastereomers improve age-related cognitive deterioration. Lipids 2012; 47 (7): 687-695.
5. Sampsona S R, Cooperb D R. Specific protein kinase C isoforms as transducers and modulators of insulin signaling. Mol Genet Metab 2006; 89 (1-2): 32-47.

(4) Transition Promoting Action of Glucose Transporter 4 (GLUT4) into Cellular Membrane GLUT4 expressed in adipocytes and skeletal muscle cells is hardly exposed on the cellular membrane in the absence of insulin stimulation, and exists in the state of being incorporated in an intracellular vesicle group. Insulin stimulation promotes transport of GLUT4 present in the intracellular vesicle onto a cellular membrane to increase the amount of GLUT4 that appears on the surface of cellular membrane, and uptake glucose into the cells to lower the blood glucose level. While promotion of sugar uptake induced by insulin is physiologically important, the physiological phenomenon in the case of diabetes is known to be disordered remarkably. When β cells in the pancreas die for some reason, insulin secretion is disordered and diabetes is developed (type 1 diabetes). At present, the sole treatment of type 1 diabetes is insulin injection from outside the body. On the other hand, marked attenuation of sugar uptake in response to insulin stimulation (insulin resistance=attenuation of insulin response) also triggers the onset of diabetes (type 2 diabetes). For the treatment of type 2 diabetes, insulin secretion stimulant, intestinal sugar absorption inhibitor, disaccharide decomposition inhibitor, DPP-4 inhibitor, PPARγ activator and the like have been used. However, the basic treatment of diabetes is promotion of cellular membrane transfer of GLUT4 via insulin/insulin receptor signal. A drug that activates intracellular downstream signals of insulin/insulin receptor and promotes transfer of GLUT4 into cellular membrane can non-insulin dependently promote intracellular sugar uptake, and is expected to show effects as a therapeutic drug for diabetes irrespective of type 1 and type 2 diabetes.

Examples of reports showing the possibility of a medicine that promotes transition of GLUT4 to a cellular membrane for application to pharmaceutical use include as follows.
1. Stockli J, Fazakerley D J, James D E. GLUT4 exocytosis. J Cell Sci 2011; 124: 4147-4159.

(5) Non-Insulin Dependent Blood Glucose Level Decreasing Action

Since the phospholipid compound of the present invention can decrease the blood glucose level without requiring insulin, it is useful for the treatment of type 2 diabetes.

While the dose of the medicine of the present invention varies depending on the target disease, severity thereof, animal species to be the administration subject, drug acceptability, body weight, age of administration subject and the like, it is generally administered to a subject in 0.5-500 mg, preferably 5-250 mg, as an amount of the phospholipid compound of the present invention which is the active ingredient, per day to an adult.

The medicine of the present invention can contain, besides the phospholipid compound of the present invention which is the active ingredient, any additive, for example, a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatic substances such as citric acid, menthol, glycyllysin•ammonium salt, glycine, orange powder and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline, orange juice and the like, base waxes such as cacao butter, polyethylene glycol, kerosene and the like, and the like.

In one embodiment, the medicine of the present invention can be formulated as a preparation preferable for oral administration. Examples of the preparation preferable for oral administration include a liquid wherein an effective amount of a substance is dissolved in a diluent such as water and saline, a capsule, granule, powder or tablet containing an effective amount of a substance as a solid or granules, a suspension wherein an effective amount of a substance is suspended in a suitable dispersion medium, an emulsion wherein a solution of an effective amount of a substance is dispersed and emulsified in a suitable dispersion medium, and the like.

In another embodiment, the medicine of the present invention can be formulated as a preparation preferable for parenteral administration. Examples of the preparation preferable for parenteral administration (e.g., intravenous injection, subcutaneous injection, muscular injection, topical injection and the like) include aqueous and nonaqueous isotonic aseptic injection liquids, which may contain antioxidant, buffer, bacteriostatic, isotonicity agent and the like. In addition, examples thereof include aqueous and non-aqueous aseptic suspensions, which may contain suspension, solubilizer, thickener, stabilizer, preservative and the like. Unit dose or plural doses of the preparation can be filled in a container such as ampoule and vial. Moreover, the active ingredient and a pharmaceutically acceptable carrier can be freeze-dried and preserved in a form that can be dissolved or suspended in a suitable aseptic vehicle immediately before use.

The phospholipid compound of the present invention can be provided as a food. The phospholipid compound of the present invention to be the active ingredient has, as mentioned above, (1) a protein tyrosine phosphatase 1B (PTP1B) inhibitory action, (2) an Akt activating action, (3) a protein phosphorylated enzyme C (PKC) activating action, (4) a PKCι and PKCζ activating action, (5) a promoting action on transition of glucose transporter 4 (GLUT4) to cellular membrane, and (6) a non-insulin-dependent blood glucose level lowering action on mammals (e.g., mouse, rat, hamster, rabbit, cat, dog, bovine, sheep, monkey, human and the like), and can be provided as functional foods effective for the prophylaxis of diseases associated with cognitive impairment, and prophylaxis of diabetes. In addition, it can be provided as a functional food expected to provide an anti-aging effect.

The "food" in the present invention means all foods and drinks other than pharmaceutical products and quasi-drugs. For example, it includes, but is not limited to, food for specified health uses, food with nutrient function claims, and what is called supplements.

The medicine of the present invention may be packed or filled individually by a unit ingestion amount or a divided amount thereof, or packed or filled comprehensively by many unit ingestion amounts or divided amounts thereof.

When the medicine of the present invention is provided as a single preparation, the unit ingestion amount of the medicine or a divided amount thereof is the unit ingestion amount of the whole phospholipid compound of the present invention or a divided amount thereof.

Examples of the pharmaceutical product or food wherein a unit ingestion amount or a divided amount thereof is packed or filled individually include general packages (e.g., PTP (press through packing) sheet, paper container, film (e.g., plastic film) container, glass container, plastic container) packed or filled with the unit ingestion amount or a divided amount thereof. The pharmaceutical products or foods that are individually packed or filled may be further combined and packed or filled in a single container (e.g., paper container, film (e.g., plastic film) container, glass container, plastic container). Examples of the pharmaceutical product or food wherein many unit ingestion amounts or a divided amount thereof are/is comprehensively packed or filled include those wherein many tablets or capsules are packed or filled in a single container (e.g., paper container, film (e.g., plastic film) container, glass container, plastic container) without distinction. The pharmaceutical product or food of the present invention may contain a unit ingestion amount or a divided amount thereof in a number sufficient for long-term ingestion. For example, a food can contain same in a number sufficient for ingestion for not less than 3 days, preferably not less than 7 days, 10 days, 14 days or 21 days, or 1 month, 2 months, or not less than 3 months.

The medicine of the present invention may contain, besides the phospholipid compound of the present invention which is an essential active ingredient, and one or more other kinds of compounds capable of preventing or treating neurodegenerative disease, or other one or more kinds of compounds capable of preventing or treating diabetes.

Examples of other compound for the prophylaxis or treatment of neurodegenerative disease include polyphenol, coenzyme Q10, β-sitosterol, isoflavone, mevinic acids, vitamin C, vitamin E, flavonoids, terpenes, folic acid, vitamin B6, vitamin B12, sesquirpene lactone, urokinase, nattokinase, dilinoleoylphosphatidylethanolamine, propyl sulfide, apple pectin, acetic acid, EPA, and DHA.

Examples of other compound capable of preventing or treating diabetes include insulin secretagogue, sulfonylurea drug, sulfoneamide drug, biguanide drug, α glucosidase inhibitor, insulin preparation, insulin sensitizer and the like. Examples thereof are nateglinide, glimepiride, glibenclamide, gliclazide, acetohexamide, tolbutamide, glycopyramide, tolazamide, glybuzole, metformin hydrochloride, buformin hydrochloride, voglibose, acarbose, insulin, pioglitazone hydrochloride and the like.

The contents disclosed in any publication cited in the present specification, including patents and patent applications, are hereby incorporated in their entireties by reference, to the extent that they have been disclosed herein.

While the present invention is explained in further detail in the following by referring to Examples and Experimental Examples, it is not limited by the following Examples and the like.

EXAMPLES (Analysis Method)

$^1$H-NMR spectrum was recorded by JEOL JNM-ECX400 spectrometer (400 MHz). As for $^1$H-NMR, the chemical shift is shown by values downfielded from TMS ($\delta$=0.00) or CHCl$_3$ ($\delta$=7.26).

ESI-MS spectrum was measured by Bruker micro TOF-Q mass spectrometer.

Column chromatography was performed on silica gel 60 (40-50 μm and 40-100 μm) (purchased from KANTO CHEMICAL CO., INC.).

All reactions were monitored using UV light, iodine and m-bromocresol green or 5% (w/v) ethanol phosphomolybdate solution and heat as color developing agents on a 0.25 mm silica gel plate 60F254 (Merck, Darmstadt, Germany).

diDCP-LA-PE can be produced by the production method described in patent document 1.

Example 1

Synthesis of diDCP-LA-PE (Step 1) Synthesis of (R)-3-benzyloxy-1,2-propanediol

To a solution of (S)-(+)-2,2-dimethyl-1,3-dioxolan-4-methanol (1.0 g, 7.6 mmol) in dimethylformamide (10 ml) were added 60% NaH (0.61 g, 15.1 mmol) and benzyl bromide (1.1 ml, 9.1 mmol) under ice-cooling.

After stirring at room temperature for 15 min, water was added to the reaction mixture. The aqueous layer was extracted with hexane, and the organic layer was washed with H$_2$O and brine. Then, it was dried over anhydrous MgSO$_4$, and concentrated under reduced pressure to give 4-benzyloxymethyl-2,2-dimethyl-1,3-dioxolane, which was used for the next step without further purification. To a solution of 4-benzyloxymethyl-2,2-dimethyl-1,3-dioxolane in methanol (17.4 ml) was added concentrated HCl (1.93 ml) under ice-cooling. After stirring at 60° C. for 30 min, a saturated aqueous NaHCO$_3$ solution was added to the reaction mixture under ice-cooling. The aqueous layer was washed with hexane, and then the aqueous layer was extracted with ethyl acetate. The organic layers were combined, dried over MgSO$_4$ and concentrated under reduced pressure to give (R)-3-benzyloxy-1,2-propanediol (1.22 g, 88%) as an oil.

$^1$H-NMR (400 MHz, CDCl$_3$): δ 3.53-3.61 (m, 2H), 3.65 (dd, J=11.4 and 5.5 Hz, 1H), 3.72 (dd, J=11.4 and 3.6 Hz, 1H), 3.88-3.93 (m, 1H), 4.56 (s, 2H), 7.30-7.39 (m, 5H).

(Step 2) Synthesis of 3-O-benzyl-1,2-O-bis-[8-{2-(2-pentyl-cyclopropylmethyl)-cyclopropyl}-octanoyl]-sn-glycerol DCP-LA (2.03 g, 6.59 mmol) was added to a solution of (R)-3-benzyloxy-1,2-propanediol (0.5 g, 2.74 mmol) in toluene, and the mixture was concentrated under reduced pressure. The obtained residue was dissolved in dichloromethane (15 ml), and 1-(3-dimethylaminopropyl)-3-ethylcarbodiimide hydrochloride (1.58 g, 8.23 mmol) and N,N-dimethylaminopyridine (0.30 g, 2.47 mmol) were added to the solution under ice-cooling. Under a nitrogen atmosphere, the mixture was stirred at room temperature for 3 hr, and 2N HCl was added to the reaction mixture. The aqueous layer was extracted three times with ethyl acetate, and the organic layers were combined and dried over anhydrous MgSO$_4$. The residue was concentrated under reduced pressure, and purified by silica gel column chromatography (hexane:ethyl acetate=20:1) to give 3-O-benzyl-1,2-O-bis-[8-{2-(2-pentyl-cyclopropylmethyl)-cyclopropyl}-octanoyl]-sn-glycerol (2.06 g, 99%) as an oil.

$^1$H-NMR (400 MHz, CDCl$_3$): δ −0.31-−0.24 (m, 4H), 0.58-0.91 (m, 18H), 0.99-1.20 (m, 5H), 1.25-1.52 (m, 37H), 1.58-1.69 (m, 2H), 2.28 (t, J=7.3 Hz, 2H), 2.33 (t, J=7.4 Hz, 2H), 3.59 (d, J=5.0 Hz, 2H), 4.19 (dd, J=11.7 and 6.9 Hz, 1H), 4.34 (dd, J=11.7 and 3.6 Hz, 1H), 4.52 (d, J=11.9 Hz, 1H), 4.57 (d, J=11.9 Hz, 1H), 5.22-5.27 (m, 1H), 7.29-7.37 (m, 5H).

(Step 3) Synthesis of 1,2-O-bis-[8-{2-(2-pentyl-cyclopropylmethyl)-cyclopropyl}-octanoyl]-sn-glycerol A solution of 3-O-benzyl-1,2-O-bis-[8-{2-(2-pentyl-cyclopropylmethyl)-cyclopropyl}-octanoyl]-sn-glycerol (1.20 g, 1.57 mmol) and 10% (w/v) palladium activated carbon (480 mg) in ethanol (80 ml) was stirred under a hydrogen atmosphere (1 atm) at room temperature for 15 min. The catalyst was removed using a celite pad, and rinsed with ethyl acetate. The combined organic layer was concentrated under reduced pressure to give 1,2-O-bis-[8-{2-(2-pentyl-cyclopropylmethyl)-cyclopropyl}-octanoyl]-sn-glycerol (1.05 g, 100%) as an oil.

$^1$H-NMR (400 MHz, CDCl$_3$): δ −0.33-0.23 (m, 4H), 0.58-0.89 (m, 12H), 0.99-1.19 (m, 6H), 1.24-1.69 (m, 44H), 2.03 (t, J=6.4 Hz, 1H), 2.32 (t, J=7.3 Hz, 2H), 2.35 (t, J=7.3 Hz, 2H), 3.73 (dd, J=6.3 and 6.4 Hz, 2H), 4.24 (dd, J=11.9 and 5.5 Hz, 1H), 4.31 (dd, J=11.9 and 4.9 Hz, 1H), 5.08 (ddd, J=6.3, 5.5 and 4.4 Hz, 1H).

(Step 4) Synthesis of diDCP-LA-PE

To a solution of 1,2-O-bis-[8-{2-(2-pentyl-cyclopropylmethyl)-cyclopropyl}-octanoyl]-sn-glycerol (1.05 g, 1.57 mmol) and triethylamine (552 ml, 3.96 mmol) in CH$_2$Cl$_2$ (40 ml) was added methyl N,N-diisopropylchlorophosphoramidite (460 ml, 2.37 mmol) under ice-cooling. After stirring at room temperature for 10 min, to the mixture were added 2-(carbobenzoxyamino)-ethanol (0.58 g, 2.97 mmol) and 1H-tetrazole (0.56 g, 7.92 mmol), 70% (v/v) aqueous solution of tert-butyl hydroperoxide (2.6 ml, 19.8 mmol) was further added, and the mixture was stirred at room temperature for 20 min. 10% (w/v) aqueous Na$_2$S$_2$O$_3$ solution was added, the obtained aqueous layer was extracted with ethyl acetate, and the organic layer was dried over anhydrous MgSO$_4$. The solution was concentrated under reduced pressure, and purified by silica gel column chromatography (hexane:ethyl acetate=4:1) to give O-[2-N-(benzyloxycarbonyl)aminoethyl] O-(1',2'-O-bis-[8-{2-(2-pentyl-cyclopropylmethyl)-cyclopropyl}-octanoyl]-sn-3'-glyceryl) O-methylphosphate (1.13 g, 68%) as an oil.

$^1$H-NMR (400 MHz, CDCl$_3$): δ −0.33--0.23 (m, 4H), 0.58-0.89 (m, 18H), 0.99-1.19 (m, 6H), 1.24-1.54 (m, 37H), 1.54-1.69 (br s, 2H), 2.32 (t, J=7.4 Hz, 2H), 2.33 (t, J=7.4 Hz, 2H), 3.42-3.56 (m, 2H), 3.75 (dd, J=11.4 and 4.6 Hz, 3H), 4.05-4.25 (m, 5H), 4.29-4.33 (m, 1H), 5.11 (s, 2H), 5.20-5.26 (m, 1H), 5.38-5.42 (m, 1H), 7.31-7.40 (m, 5H); ESI-HRMS (negative ion, sodium formate) calculated for C$_{54}$H$_{90}$NO$_{10}$PNa ([M+Na]$^+$) 966.6191; found 966.6089.

To a solution of O-[2-N-(benzyloxycarbonyl)aminoethyl] O-(1',2'-O-bis-[8-{2-(2-pentyl-cyclopropylmethyl)-cyclopropyl}-octanoyl]-sn-3'-glyceryl) O-methylphosphate (1.2 g, 1.6 mmol) in 2-butanone (23 ml) was added NaI (899 mg, 6.0 mmol). After stirring at 80° C. for 1 hr, 2N HCl was added to the reaction mixture, and the aqueous layer was extracted with chloroform. The organic layer was washed with H$_2$O and brine, and the combined organic layer was dried over anhydrous MgSO$_4$ and concentrated under reduced pressure to give O-[2-N-(benzyloxycarbonyl)aminoethyl] O-(1',2'-O-bis-[8-{2-(2-pentyl-cyclopropylmethyl)-cyclopropyl}-octanoyl]-sn-3'-glyceryl)phosphate.

To a solution of O-[2-N-(benzyloxycarbonyl)aminoethyl] O-(1',2'-O-bis-[8-{2-(2-pentyl-cyclopropylmethyl)-cyclopropyl}-octanoyl]-sn-3'-glyceryl)phosphate in methanol (120 ml) was added 10% (w/v) palladium on activated carbon (500 mg). The obtained suspension was stirred under a hydrogen atmosphere (1 atm) at room temperature for 24 hr. The catalyst was removed using a celite pad, rinsed with ethyl acetate, and concentrated under reduced pressure. The obtained crude product was purified by silica gel column chromatography (chloroform:methanol=10:1) to give 1,2-o-bis-[8-{2-(2-pentyl-cyclopropylmethyl)-cyclopropyl)-octanoyl}-sn-glycero-3-phosphatidylethanolamine (0.60 g, 70%) as a yellow oil.

$^1$H-NMR (400 MHz, C$_6$D$_5$N): δ −0.16--0.08 (m, 4H), 0.69-0.99 (m, 18H), 1.16-1.59 (m, 45H), 1.64-1.80 (m, 5H), 2.43 (t, J=7.8 Hz, 2H), 2.48 (t, J=6.4 Hz, 2H), 3.56-3.64 (br s, 2H), 4.33-4.45 (m, 2H), 4.53 (dd, J=11.9 Hz, 1H), 4.56-4.69 (br s, 2H), 4.73 (dd, J=9.6 and 2.7 Hz, 1H), 6.87 (d, J=9.2 Hz, 1H), 6.91 (dd, J=8.2 and 1.8 Hz, 1H), 7.00 (d, J=1.8 Hz, 1H), 7.03 (d, J=2.3 Hz, 1H), 7.16 (d, J=1.8 Hz, 1H), 7.47 (d, J=8.3 Hz, 2H), 7.67 (d, J=8.3 Hz, 2H);

ESI-HRMS (negative ion, sodium formate) calculated for C$_{45}$H$_{82}$NO$_8$PNa$^+$ ([M+Na]$^+$) 818.5670; found 818.5652.

Example 2

Synthesis of diDCP-LA-PS

To a solution of 1,2-O-bis-[8-{2-(2-pentyl-cyclopropylmethyl)-cyclopropyl}-octanoyl]-sn-glycerol (0.44 g, 0.66 mmol) and triethylamine (0.18 ml, 1.3 mmol) in CH$_2$Cl$_2$ (15 ml) was added methyl N,N-diisopropylchlorophosphoramidite (0.15 ml, 0.79 mmol) under ice-cooling. After stirring at room temperature for 10 min, to the mixture were added N-carbobenzoxy-serine benzyl ester (0.33 g, 0.99 mmol) and 1H-tetrazole (0.19 g, 2.6 mmol), 70% (v/v) aqueous solution of tert-butyl hydroperoxide (0.87 ml, 6.6 mmol) was further added, and the mixture was stirred at the same temperature for 20 min. 10% (w/v) aqueous Na$_2$S$_2$O$_3$ solution was added, the obtained aqueous layer was extracted with ethyl acetate, and the organic layer was dried over anhydrous MgSO$_4$. The solution was concentrated under reduced pressure, and purified by silica gel column chromatography (hexane:ethyl acetate=3:1) to give O-[N-(benzyloxycarbonyl)-L-serine benzyl ester] O-(1,2-O-bis-[8-{2-(2-pentyl-cyclopropylmethyl)-cyclopropyl}-octanoyl]-sn-3-glyceryl) O-methylphosphate (490 mg, 68%) as a colorless oil.

$^1$H-NMR (400 MHz, CDCl$_3$): δ −0.33--0.20 (m, 4H), 0.55-0.85 (m, 12H), 0.87-0.95 (m, 6H), 0.96-1.70 (m, 44H), 2.30 (t, J=7.3 Hz, 2H), 2.31 (t, J=7.3 Hz, 2H), 3.65 (dd, J=11.5 and 2.8 Hz, 3H), 4.00-4.20 (m, 3H), 4.21-4.41 (m, 2H), 4.42-4.49 (m, 1H), 4.59-4.65 (m, 1H), 5.13 (s, 2H), 5.14-5.20 (m, 1H), 5.21 (s, 2H), 5.93 (dd J=8.2 and 8.2 Hz, 1H), 7.20-7.44 (m, 10H);

ESI-HRMS (positive ion, sodium formate) calculated for C$_{62}$H$_{96}$NO$_{12}$PNa ([M+H]$^-$) 1100.6562; found 1100.6307.

To a solution of O-[N-(benzyloxycarbonyl)-L-serine benzyl ester] O-(1,2-O-bis-[8-{2-(2-pentyl-cyclopropylmethyl)-cyclopropyl}-octanoyl]-sn-3-glyceryl) O-methylphosphate (200 mg, 0.19 mmol) in 2-butanone (3 ml) was added NaI (139 mg, 0.93 mmol). After stirring at 80° C. for 1 hr, 2N HCl was added to the reaction mixture, and the aqueous layer was extracted with chloroform. The organic layer was washed with H$_2$O and brine, and the combined organic layer was dried over anhydrous MgSO$_4$ and concentrated under reduced pressure to give O-[N-(benzyloxycarbonyl)-L-serine benzyl ester] O-(1,2-O-bis-[8-{2-(2-pentyl-cyclopropylmethyl)-cyclopropyl}-octanoyl]-sn-3-glyceryl)phosphate.

To a solution of O-[N-(benzyloxycarbonyl)-L-serine benzyl ester] O-(1,2-O-bis-[8-{2-(2-pentyl-cyclopropylmethyl)-cyclopropyl}-octanoyl]-sn-3-glyceryl)phosphate in ethanol (30 ml) was added 10% (w/v) palladium on activated carbon (72 mg). The obtained suspension was stirred under a hydrogen atmosphere (1 atm) at room temperature for 2 hr. The obtained crude product was purified by silica gel column chromatography (chloroform:methanol=10:1) to give 1,2-O-bis-[8-{2-(2-pentyl-cyclopropylmethyl)-cyclopropyl}-octanoyl]-sn-glycero-3-phosphatidyl-L-serine (50 mg, 31%) as a white solid.

$^1$H-NMR (400 MHz, CDCl$_3$): δ−0.30--0.20 (m, 4H), 0.55-0.85 (m, 12H), 0.87-0.95 (m, 6H), 0.96-1.70 (m, 44H), 2.25-2.43 (m, 4H), 3.80-4.30 (m, 4H), 4.32-4.51 (m, 2H), 5.20-5.32 (m, 1H); ESI-HRMS (negative ion, sodium formate) calculated for $C_{46}H_{81}NO_{10}P$ ($[M-H]^-$) 838.5604; found 838.5599.

Example 3

Synthesis of diDCP-LA-PC

To a solution of 1,2-O-bis-[8-(2-{2-pentyl-cyclopropylmethyl)-cyclopropyl}-octanoyl]-sn-glycerol (0.14 g, 0.21 mmol) and triethylamine (0.058 ml, 0.42 mmol) in $CH_2Cl_2$ (5 ml) was added methyl N,N-diisopropylchlorophosphoramidite (0.048 ml, 0.25 mmol) under ice-cooling.

After stirring at room temperature for 10 min, to the mixture were added 2-chloroethanol (0.025 g, 0.31 mmol) and 1H-tetrazole (0.058 g, 0.42 mmol), 70% (v/v) aqueous solution of tert-butyl hydroperoxide (0.27 ml, 2.1 mmol) was further added, and the mixture was stirred at the same temperature for 20 min. 10% (w/v) aqueous $Na_2S_2O_3$ solution was added, and the obtained aqueous layer was extracted with $CH_2Cl_2$. The combined organic layer was dried over anhydrous $MgSO_4$, and concentrated under reduced pressure. The crude product was purified by silica gel column chromatography (hexane:ethyl acetate=3:1) to give O-(1,2-O-bis-[8-{2-(2-pentyl-cyclopropylmethyl)-cyclopropyl}-octanoyl]-sn-3-glyceryl) O-(2'-chloroethyl) O-methylphosphate (107 mg, 60%) as a colorless oil.

$^1$H-NMR (400 MHz, $CDCl_3$): δ −0.33--0.20 (m, 4H), 0.55-0.85 (m, 12H), 0.87-0.95 (m, 6H), 0.96-1.72 (m, 44H), 2.32 (t, J=7.8 Hz, 2H), 2.34 (t, J=7.8 Hz, 2H), 3.70 (t, J=6.5 Hz, 2H), (dd, J=11.5 and 2.8 Hz, 3H), 4.10-4.40 (m, 6H), 5.25 (ddd J=5.0, 5.0 and 5.0 Hz, 1H); ESI-HRMS (positive ion, sodium formate) calculated for $C_{46}H_{82}ClO_8PNa$ ($[M+Na]^+$) 851.5334; found 851.5283.

To a solution of O-(1,2-O-bis-[8-{2-(2-pentyl-cyclopropylmethyl)-cyclopropyl}-octanoyl]-sn-3-glyceryl) O-(2'-chloroethyl) O-methylphosphate (100 mg, 0.19 mmol) in $CH_3CN$ (3 ml) was added trimethylamine (5 ml) under dry ice-cooling. After stirring at 70° C. for 7 hr, the reaction mixture was cooled to room temperature and concentrated under reduced pressure. The obtained crude product was purified by silica gel column chromatography (chloroform:methanol=20:1) to give 1,2-O-bis-[8-{2-(2-pentyl-cyclopropylmethyl)-cyclopropyl}-octanoyl]-sn-3-glycero-3-phosphatidylcholine (15 mg, 18%) as a white solid.

$^1$H-NMR (400 MHz, $CDCl_3$): δ −0.33--0.20 (m, 4H), 0.55-0.84 (m, 12H), 0.87-0.95 (m, 6H), 0.96-1.72 (m, 44H), 2.32 (t, J=7.8 Hz, 2H), 2.34 (t, J=7.8 Hz, 2H), 3.23 (s, 9H), 3.60-3.70 (m, 4H), 4.00 (m, 2H), 4.20 (m, 1H), 4.25-4.40 (m, 2H), 4.45 (m, 1H), 5.26 (m, 1H); ESI-HRMS (negative ion, sodium formate) calculated for $C_{48}H_{89}NO_8P$ ($[M+H]^+$) 838.6320; found 838.6310.

Example 4

Synthesis of diDCP-LA-D-PI

To a solution of 1,2-O-bis-[8-{2-(2-pentyl-cyclopropylmethyl)-cyclopropyl}-octanoyl]-sn-glycerol (0.080 g, 0.12 mmol) and triethylamine (0.033 ml, 0.24 mmol) in $CH_2Cl_2$ (2 ml) was added methyl N,N-diisopropylchlorophosphoramidite (0.028 ml, 0.14 mmol) under ice-cooling. After stirring at room temperature for 10 min, to the mixture were added (−)-2,3,4,5,6-penta-O-benzyl-D-1-inositol (0.11 g, 0.18 mmol) and 1H-tetrazole (0.033 g, 0.48 mmol), 70% (v/v) aqueous solution of tert-butyl peroxide (0.16 ml, 1.2 mmol) was further added, and the mixture was stirred at the same temperature for 20 min. 10% (w/v) aqueous $Na_2S_2O_3$ solution was added, and the obtained aqueous layer was extracted with $CH_2Cl_2$. The combined organic layer was dried over anhydrous $MgSO_4$, and concentrated under reduced pressure. The crude product was purified by silica gel column chromatography (hexane:ethyl acetate=1:1) to give O-(1,2-O-bis-[8-{2-(2-pentyl-cyclopropylmethyl)-cyclopropyl}-octanoyl]-sn-3-glyceryl) O-methyl O-(2',3',4',5',6'-penta-O-benzyl-D-1'-inositol)phosphate (30 mg, 17%) as a white solid.

$^1$H-NMR (400 MHz, $CDCl_3$): δ −0.33--0.21 (m, 4H), 0.52-0.85 (m, 12H), 0.87-0.95 (m, 6H), 0.96-1.70 (m, 44H), 2.24 (t, J=7.3 Hz, 2H), 2.26 (t, J=7.3 Hz, 2H), 3.46-3.54 (m, 2H), 3.67 (d, J=11.4 Hz, 3H), 3.88 (dd, J=11.9 and 6.0 Hz, 1H), 3.94 (ddd, J=6.8, 6.4 and 5.0 Hz, 1H), 4.00-4.15 (m, 4H), 4.24 (ddd, J=7.7, 7.4 and 2.1 Hz, 1H), 4.34 (t, J=2.1 Hz, 1H), 4.67 (d, J=11.4 Hz, 1H), 4.73 (d, J=11.4 Hz, 1H), 4.75-4.85 (m, 4H), 4.85-4.95 (m, 3H), 4.95 (d, J=11.4 Hz, 1H), 5.00-5.07 (m, 1H).

To a solution of O-(1,2-O-bis-[8-{2-(2-pentyl-cyclopropylmethyl)-cyclopropyl}-octanoyl]-sn-3-glyceryl) O-methyl O-(2',3',4',5',6'-penta-O-benzyl-D-1'-inositol) phosphate (30 mg, 0.020 mmol) in 2-butanone (2 ml) was added NaI (0.017 g, 0.11 mmol). The mixture was stirred at 80° C. for 2 hr, 2N HCl was added to the reaction mixture, and the aqueous layer was extracted with chloroform. The organic layer was washed with $H_2O$ and brine, and the combined organic layer was dried over anhydrous $MgSO_4$, and concentrated under reduced pressure to give O-(1,2-O-bis-[8-{2-(2-pentyl-cyclopropylmethyl)-cyclopropyl}-octanoyl]-sn-3'-glyceryl) O-methyl O-(2',3',4',5',6'-penta-O-benzyl-D-1'-inositol)phosphate. To a solution of O-(1,2-O-bis-[8-{2-(2-pentyl-cyclopropylmethyl)-cyclopropyl}-octanoyl]-sn-3'-glyceryl) O-methyl O-(2',3',4',5',6'-penta-O-benzyl-D-1'-inositol)phosphate in ethanol (3 ml) was added 10% (w/v) palladium on activated carbon (21 mg). The obtained suspension was stirred under a hydrogen atmosphere (1 atm) at room temperature for 2 hr. The catalyst was removed using a celite pad, rinsed with ethyl acetate, and concentrated under reduced pressure. The obtained crude product was purified by silica gel column chromatography (chloroform:methanol=10:1) to give 1,2-O-bis-[8-{2-(2-pentyl-cyclopropylmethyl)-cyclopropyl}-octanoyl]-sn-glycero-3-phosphatidyl-D-1-inositol (10 mg, 55%) as a white solid.

$^1$H-NMR (400 MHz, $CDCl_3$): δ −0.33--0.20 (m, 4H), 0.55-0.85 (m, 12H), 0.87-0.95 (m, 6H), 0.96-1.70 (m, 44H), 2.20-2.43 (m, 4H), 3.80-4.51 (m, 5H), 5.18-5.32 (m, 1H); ESI-HRMS (negative ion, sodium formate) calculated for $C_{49}H_{86}O_{13}P$ ($[M-H]^-$) 913.5811; found 913.5806.

Example 5

Synthesis of Non-Natural Type diDCP-LA-L-PI

To a solution of 1,2-O-bis-[8-{2-(2-pentyl-cyclopropylmethyl)-cyclopropyl}-octanoyl]-sn-glycerol (0.175 g, 0.26 mmol) and triethylamine (0.072 ml, 0.52 mmol) in $CH_2Cl_2$ (5 ml) was added methyl N,N-diisopropylchlorophosphoramidite (0.061 ml, 0.31 mmol) under ice-cooling. After stirring at room temperature for 10 min, to the mixture were added (+)-2,3,4,5,6-penta-O-benzyl-L-1-inositol (0.25 g, 0.39 mmol) and 1H-tetrazole (0.073 g, 1.04 mmol), 70% (v/v) aqueous solution of tert-butyl peroxide (0.34 ml, 2.6 mmol) was further added, and the mixture was stirred at the same temperature for 20 min. 10% (w/v) aqueous $Na_2S_2O_3$ solution was added, and the obtained aqueous layer was extracted with CH$_2$Cl$_2$. The combined organic layer was dried over anhydrous MgSO$_4$, and concentrated under reduced pressure. The crude product was purified by silica gel column chromatography (toluene:ethyl acetate=6:1) to give O-(1,2-O-bis-[8-{2-(2-pentyl-cyclopropylmethyl)-cyclopropyl}-octanoyl]-sn-3-glyceryl) O-methyl O-(2',3',4',5',6'-penta-O-benzyl-L-1'-inositol)phosphate (90 mg, 25%) as a white solid.

$^1$H-NMR (400 MHz, CDCl$_3$): δ −0.33--0.21 (m, 4H), 0.52-0.85 (m, 12H), 0.87-0.95 (m, 6H), 0.96-1.70 (m, 44H), 2.25 (t, J=7.3 Hz, 2H), 2.26 (t, J=7.3 Hz, 2H), 3.46-3.54 (m, 2H), 3.61 (d, J=11.4 Hz, 3H), 3.94 (dd, J=11.9 and 6.0 Hz, 1H), 4.00-4.32 (m, 7H), 4.68 (d, J=11.9 Hz, 1H), 4.72 (d, J=11.9 Hz, 1H), 4.73-4.85 (m, 8H), 5.15-5.25 (m, 1H).

To a solution of O-(1,2-O-bis-[8-{2-(2-pentyl-cyclopropylmethyl)-cyclopropyl}-octanoyl]-sn-3-glyceryl) O-methyl O-(2',3',4',5',6'-penta-O-benzyl-L-1-inositol) phosphate (90 mg, 0.070 mmol) in 2-butanone (2 ml) was added NaI (50 mg, 0.33 mmol). After stirring at 80° C. for 3 hr, 2N HCl was added to the reaction mixture, and the aqueous layer was extracted with chloroform. The organic layer was washed with H$_2$O and brine, and the combined organic layer was dried over anhydrous MgSO$_4$ and concentrated under reduced pressure to give O-(1,2-O-bis-[8-{2-(2-pentyl-cyclopropylmethyl)-cyclopropyl}-octanoyl]-sn-3-glyceryl) O-methyl O-(2',3',4',5',6'-penta-O-benzyl-L-1-inositol)phosphate. To a solution of O-(1,2-O-bis-[8-{2-(2-pentyl-cyclopropylmethyl)-cyclopropyl}-octanoyl]-sn-3-glyceryl) O-methyl O-(2',3',4',5',6'-penta-O-benzyl-L-1-inositol)phosphate in ethanol (5 ml) was added 10% (w/v) palladium on activated carbon (70 mg). The obtained suspension was stirred under a hydrogen atmosphere (1 atm) at room temperature for 2 hr. The catalyst was removed using a celite pad, rinsed with ethyl acetate, and concentrated under reduced pressure. The obtained crude product was purified by silica gel column chromatography (chloroform: methanol=10:1) to give 1,2-O-bis-[8-{2-(2-pentyl-cyclopropylmethyl)-cyclopropyl}-octanoyl]-sn-glycero-3-phosphatidyl-L-1-inositol (20 mg, 43%) as a white solid.

$^1$H-NMR (400 MHz, CDCl,): δ −0.33--0.20 (m, 4H), 0.55-0.85 (m, 12H), 0.87-0.95 (m, 6H), 0.96-1.70 (m, 44H), 2.20-2.43 (m, 4H), 3.50-4.51 (m, 5H), 5.10-5.42 (m, 1H); ESI-HRMS (negative ion, sodium formate) calculated for C$_{49}$H$_{86}$O$_{13}$P ([M−H]$^−$) 913.5811; found 913.5811.

Experimental Example 1

Protein Tyrosine Phosphatase 1B (PTP1B) Inhibitory Action (Material and Method)
Assay of PTP1B Activity Under Cell-Free Conditions Protein tyrosine phosphatase was measured under cell-free conditions by a method partially modified from the methods described in previous reports (Baba Y, et al. J Am Chem Soc 2003; 125; 9740-9749; Rice R L, et al. Biochemistry 1997; 36: 15965-15974). Human PTP1B was cloned to a pGEX-6P-3 vector having a GST tag at the NH$_2$ terminal, and expressed in competent E. coli BL21(DE3) suitable for transformation and protein expression. GST fusion PTP1B was affinity-purified using glutathione sepharose 4B (GE Healthcare Bio-Science KK, Tokyo, Japan). It was reacted with p-nitrophenylphosphate (p-NPP) (Sigma, St. Louis, Mo., USA) as a substrate and PTP1B activity was measured. The enzyme was pre-incubated in a reaction medium [50 mM HEPES, 1 mM EDTA, 50 mM NaCl, 1 mM dithiothreitol, pH 7.2] at 37° C. for 30 min in the presence or absence of diDCP-LA-PE and with or without addition of Na$_3$VO$_4$ which is a PTP1B inhibitor. Then, p-NPP (10 mM) was added to the reaction medium, and the mixture was incubated for 60 min. The reaction was discontinued by the addition of 0.1N NaOH. Dephosphorylated p-NPP, i.e., p-NP, was quantified at an absorbance of 405 nm by using SpectraMax PLUS384 (Molecular Devices, Sunnyvale, Calif., USA).

Figure 2:
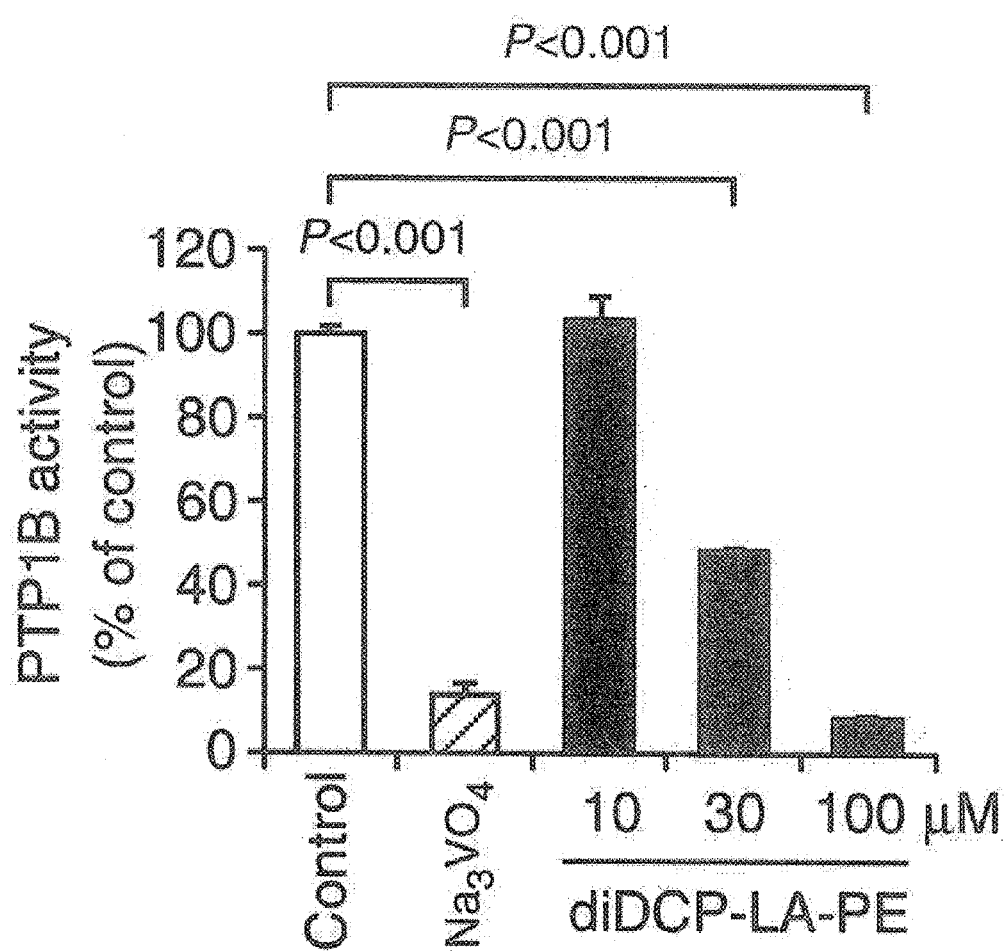
FIG. 2 is a graph showing induction of protein tyrosine phosphatase (PTP1B) inhibition by diDCP-LA-PE. PTP1B was reacted with p-NPP under cell-free conditions in the presence and absence of $Na_3VO_4$ (10 μM), and dephosphorylated p-NPP was quantified. In the graph, each column shows mean (±SD) percentage to the phosphatase activity to be the standard (control) (n=4 in each experiment). P value, Dunnett's test.

(Results)
The results are shown in FIG. 2.

Figure 3:
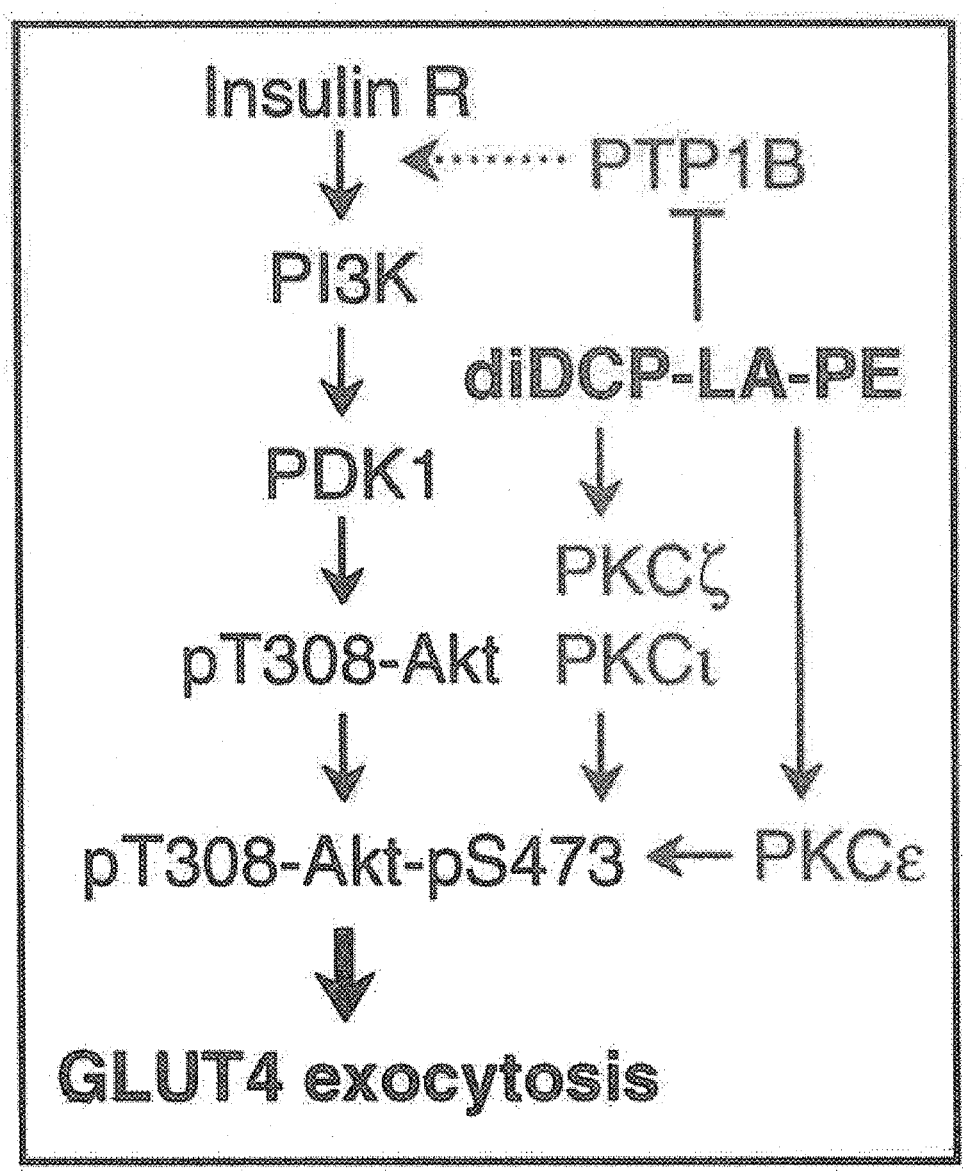
FIG. 3 shows a membrane transport signal pathway of GLUT4 by diDCP-LA-PE. Since diDCP-LA-PE inhibits PTP1B, tyrosine kinase is indirectly activated to promote cellular membrane transport of GLUT4.

The results show that diDCP-LA-PE inhibits PTP1B in a concentration-dependent manner. This further suggests that diDCP-LA-PE indirectly activates tyrosine kinase (reference pathway is shown in FIG. 3).

Experimental Example 2

Akt Activating Action (Material and Method)
1. Cell Culture

3T3L1-GLUT4myc fibroblast strain expressing GLUT4myc was used. The cells are constructed by inserting human c-MYC epitope (14 amino acids) into the first ectodomain. The cells were cultured in Dulbecco's Modified Eagles Medium (DMEM) added with 10% (v/v) bovine serum, penicillin (final concentration, 100 U/ml) and streptomycin (final concentration, 0.1 mg/ml) in a humid environment under 5% CO$_2$ and 95% air at 37° C. When the cells reached confluence (day 0), the medium was exchanged with DMEM added with 10% (v/v) fetal bovine serum (FBS), 1 μM dexamethasone, 0.5 mM 3-isobutyl-methylxanthine and 0.1 mg/ml insulin to allow for differentiation from fibroblast into adipocyte. The medium was exchanged with DMEM added with 10% (v/v) FBS on day 3, day 7 and day 11. On day 14, the cells were used for the experiment.

2. Western Blotting

3T3L1-GLUT4myc adipocytes were incubated in Krebs-Ringer-HEPES buffer [136 mM NaCl, 4.7 mM KCl, 1.25 mM CaCl$_2$, 1.25 mM MgSO$_4$ and 20 mM HEPES, pH 7.5] containing 0.2% (w/v) bovine serum albumin and added with 10 mM glucose at 37° C. for 1 hr. The cells were incubated in the presence or absence of diDCP-LA-PE for 20 min. Then, the cells were lysed in a lysis buffer [150 mM NaCl, 20 mM ethylenediaminetetraacetic acid, 0.5% (v/v) Nonidet P-40 and 50 mM Tris, pH 7.4] containing 1% (v/v) protease inhibitor cocktail, and centrifuged at 4° C. for 5 min at 3,000 rpm. The supernatant was used as a total cell lysate.

For Western blotting, the protein was separated by SDS-polyacrylamide gel electrophoresis (SDS-PAGE), and transferred onto polyvinylidene difluoride membranes. The blotting membranes were blocked with TBS-T [150 mM NaCl, 0.1% (v/v) Tween20 and 20 mM Tris, pH 7.5] containing 5% (w/v) BSA, and sequentially reacted with antibodies (Cell Signaling Technology, Inc., Danvers, Mass., USA) against phospho-Akt (Thr308), phospho-Akt (Ser473) and Akt. After washing, the membranes were reacted with horseradish peroxidase conjugate goat anti-rabbit IgG antibody. The immunoreactivity was detected using ECL kit (GE Healthcare, Piscataway, N.J., USA), and visualized using a chemical luminescence detection system (chemiluminescence detection system; GE Healthcare). The protein concentration of each sample was measured using BCA protein assay kit (Thermo Fisher Scientific, Waltham, Mass., USA).

Figure 4:
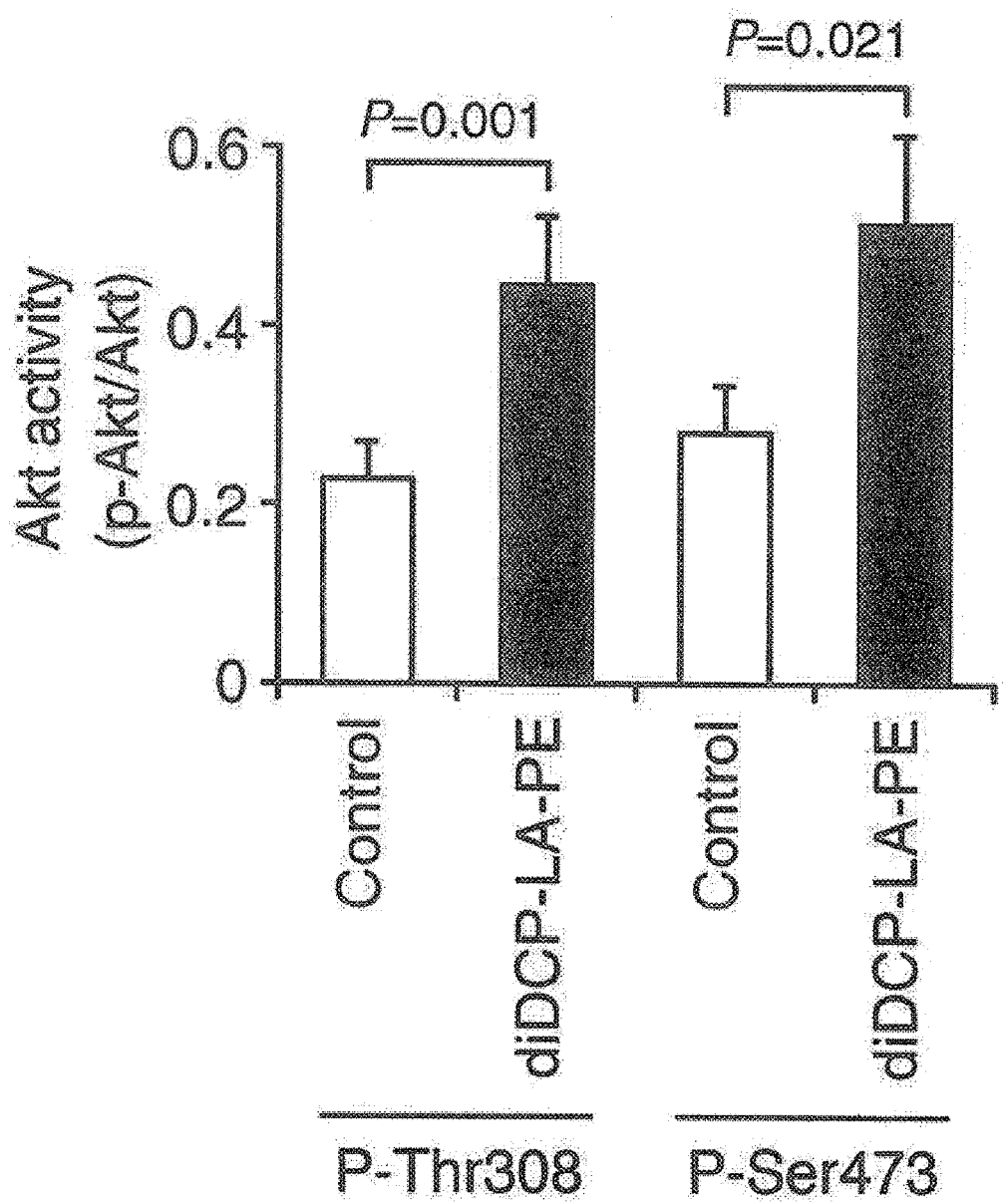
FIG. 4 is a graph showing induction of Akt activation by diDCP-LA-PE. 3T3L1-GLUT4myc cells were treated for 10 min with or without diDCP-LA-PE (1 μM), after which Western blotting was performed using antibodies to phospho-threonine 308 (P-Thr308), phospho-serine 473 (P-Ser473) and Akt. The signal intensity of P-Thr308 or P-Ser473 was normalized against the signal intensity of Akt. In the graph, each column shows mean (±SEM) proportion of phosphorylated Akt relative to the total Akt (n=4 in each experiment). P value, unpaired t-test.

(Results)
The results are shown in FIG. 4.

The results show that diDCP-LA-PE has an action to activate Akt (Akt is activated by phosphorylation of Thr308 and Ser473).

Experimental Example 3

PKC Activating Action (Material and Method)
Cell-Free PKC AAssay

PKC activity in a cell-free system was quantified by the method described in a previous report (Kanno T et al. J Lipid Res 2006; 47: 1146-1156). In short, synthesized PKC substrate peptide (10 µM) was reacted with various PKC isozymes in a medium containing 20 mM Tris-HCl (pH 7.5), 5 mM magnesium acetate, 10 µM ATP, and DCP-LA-phospholipid in the absence of phosphatidylserine and diacylglycerol at 30° C. for 5 min. A $Ca^{2+}$-free medium was used for novel PKC such as PKC-δ, -ε and the like, and a 100 µM $CaCl_2$-containing medium was used for other PKC isozymes. They were loaded on reversed-phase HPLC (LC-10ATvp, Shimadzu Co., Kyoto, Japan), and the peaks of substrate peptide and new resultant products were measured at an absorbance of 214 nm. The areas of non-phosphorylated PKC substrate peptide and phosphorylated PKC substrate peptide were measured (total area corresponds to the concentration of PKC substrate peptide used in this Example), and the amount of the phosphorylated substrate peptide was calculated. The amount of the phosphorylated substrate peptide (pmol/1 min) per 1 min was used as an index of the PKC activity.

(Results)

Figure 5:
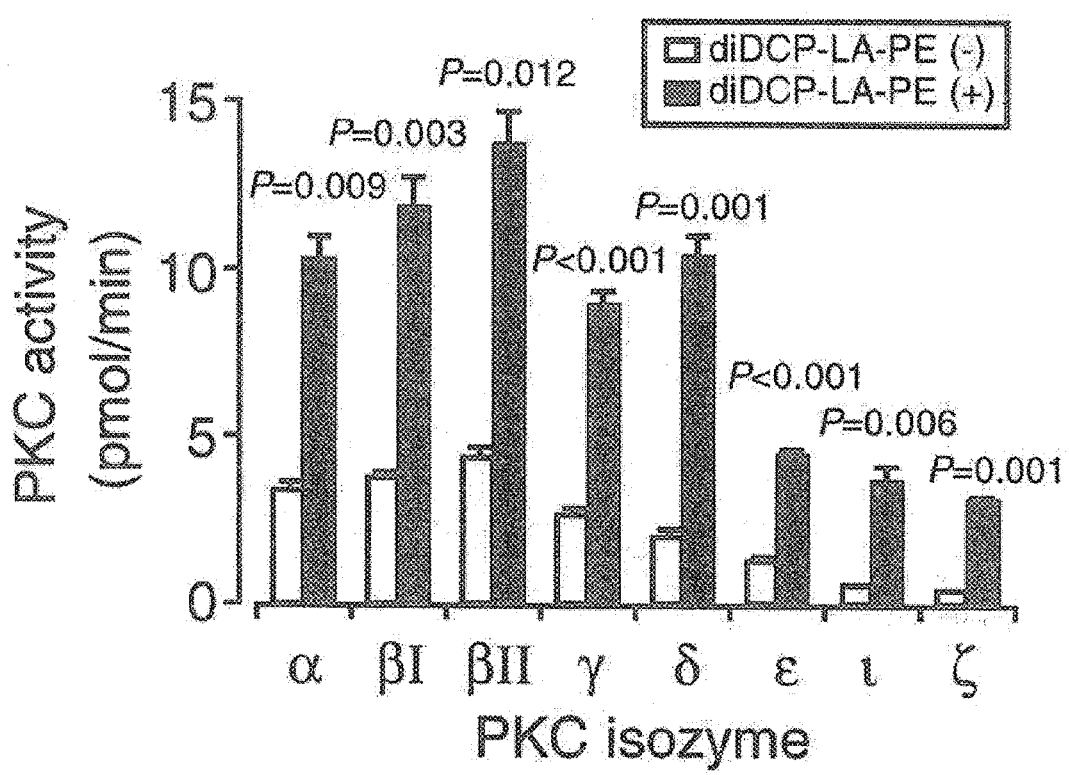
FIG. 5 is a graph showing induction of PKC activation by diDCP-LA-PE. PKC activity was monitored in a cell-free system. Given PKC isozymes were evaluated in the absence (control) or presence of diDCP-LA-PE (100 μM). In the graph, each column shows mean (±SEM) PKC activity (pmol/min) (n=6). P value, as compared to PKC isozyme activation in the absence of diDCP-LA-PE, Dunnett's test.
Figure 6:
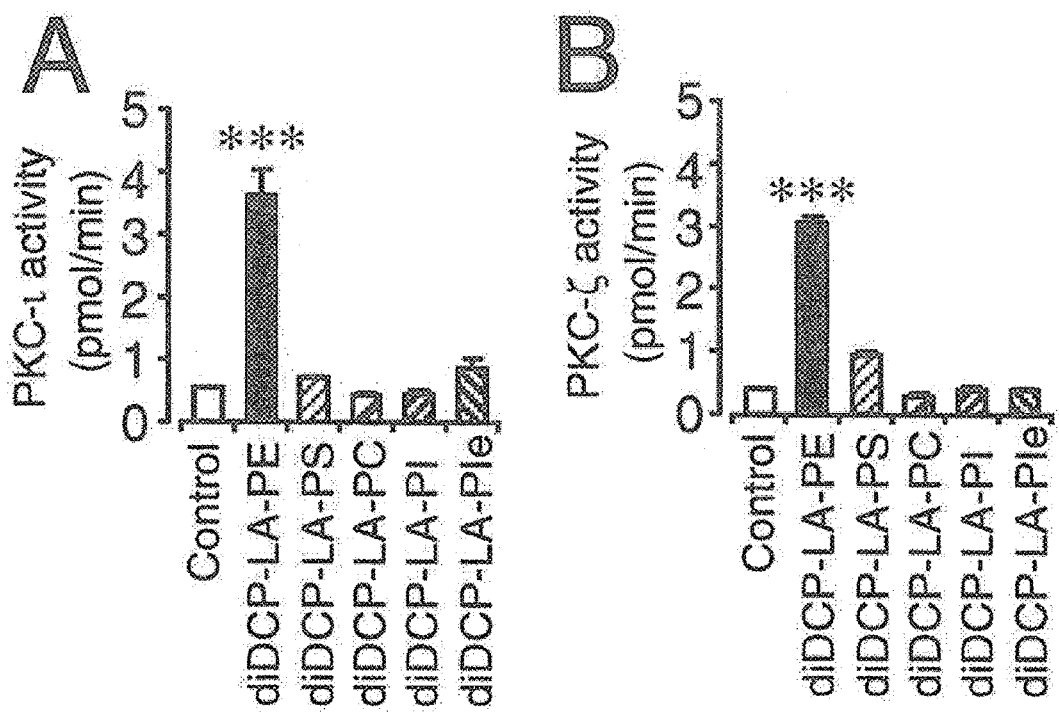
FIG. 6 is a graph showing that diDCP-LA-PE is a specific activator of PKCι and PKCζ. Given PKC isozymes were evaluated in the presence of diDCP-LA-PE (100 μM), diDCP-LA-PS (100 μM), diDCP-LA-PC (100 μM), diDCP-LA-PI (100 μM) or diDCP-LA-PI enantiomer (diDCP-LA-PIe) (100 μM). In the graph, each column shows mean (±SEM) PKCι or PKCζ activity (pmol/min) (n=4). ***$P<0.001$ (other than diDCP-LA-PE), as compared to PKCι or PKCζ activation induced by each phospholipid derivative, Dunnett's test.

The results are shown in FIGS. 5 and 6. FIG. 5 shows that diDCP-LA-PE activates all PKC isozymes. FIG. 6 shows that diDCP-LA-PE functions as a specific activating agent of PKCι and PKCζ considered to be important for the adjustment of GLUT4 trafficking.

Experimental Example 4

Promoting Action on Transfer of Sugar Transport Carrier GLUT4 to Cellular Membrane-1

(Material and Method)
Analysis of GLUT4 Trafficking

3T3L1-GLUT4myc adipocytes were incubated in Krebs-Ringer-HEPES buffer [136 mM NaCl, 4.7 mM KCl, 1.25 mM $CaCl_2$, 1.25 mM $MgSO_4$ and 20 mM HEPES, pH 7.5] containing 0.2% (w/v) bovine serum albumin and added with 10 mM glucose at 37° C. for 1 hr. The cells were incubated in the presence or absence of insulin, phospholipid or a derivative thereof for 20 min. Then, the cells were homogenized by sonication in an ice-cooled mitochondria buffer containing 1% (v/v) protease inhibitor cocktail [210 mM mannitol, 70 mM sucrose, and 1 mM ethylenediaminetetraacetic acid (EDTA), 10 mM HEPES, pH 7.5]. Sequentially, the homogenate was centrifuged at 4° C. for 5 min at 3,000 rpm. The supernatant was further centrifuged at 4° C. for 15 min at 11,000 rpm. The recovered supernatant was ultracentrifuged at 4° C. for 60 min at 100,000 g, and separated into a cytoplasm fraction and a cellular membrane fraction. The supernatant was used as the cytoplasm fraction and the pellet was used as the cellular membrane fraction. Whether the cytoplasm component and the cellular membrane component could be successfully separated was confirmed by Western blot analysis using an antibody to LDH which is a cellular membrane component marker, and an antibody to cadherin which is a cellular membrane marker. The protein concentration of each fraction was measured using BCA protein assay kit (Thermo Fisher Scientific, Waltham, Mass., USA). The protein of the cellular membrane fraction was resuspended in a mitochondria buffer containing 1% (w/v) sodium dodecyl sulfate (SDS). The protein of each fraction was separated by SDS-polyacrylamide gel electrophoresis (SDS-PAGE), and transferred onto polyvinylidene difluoride membranes. The blotting membranes were blocked with TBS-T [150 mM NaCl, 0.1% (v/v) Tween20 and 20 mM Tris, pH 7.5] containing 5% (w/v) BSA, reacted with anti-c-myc antibody (Merck Millipore, Darmstadt, Germany), and thereafter reacted with horseradish peroxidase (HRP) conjugate goat anti-mouse IgG antibody. The immunoreactivity was detected using ECL kit (Invitrogen), and visualized using a chemical luminescence detection system (chemiluminescence detection system; GE Healthcare, Piscataway, N.J., USA). The signal density was measured using an image analysis software (Image Gauge software; GE Healthcare).

(Results)

Figure 7:
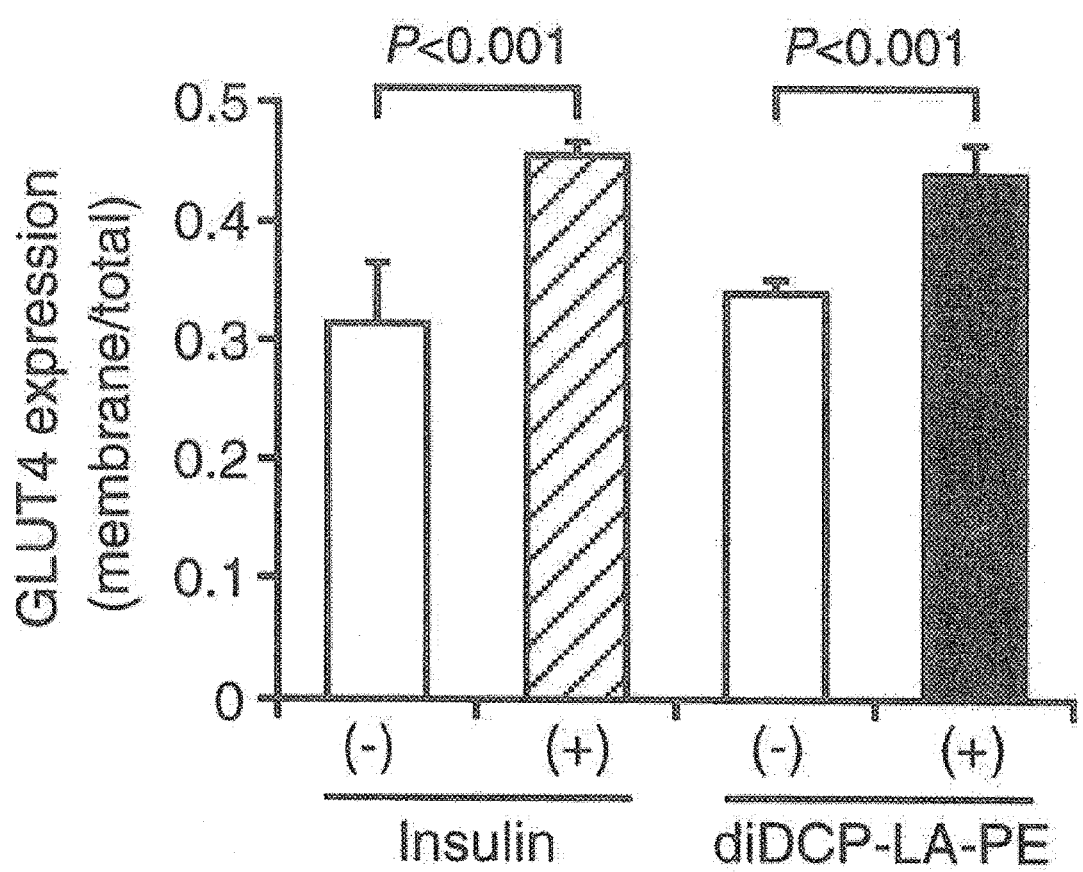
FIG. 7 is a graph showing that diDCP-LA-PE promotes cellular membrane transport of GLUT4 in differentiated 3T3L1-GLUT4 myc adipocytes. Without treatment with insulin or diDCP-LA-PE (1 μM), or 20 min after the treatment, the cells were lysed and divided into cytoplasm fraction and cellular membrane fraction, and Western blotting was performed using an anti-c-myc antibody. In the graph, each column shows mean (±SD) ratio of signal intensity of GLUT4 in cellular membrane fraction/signal intensity of GLUT4 in the whole cellular membrane fraction and cytoplasm fraction (n=6 in each experiment). P value, unpaired t-test.
Figure 8:
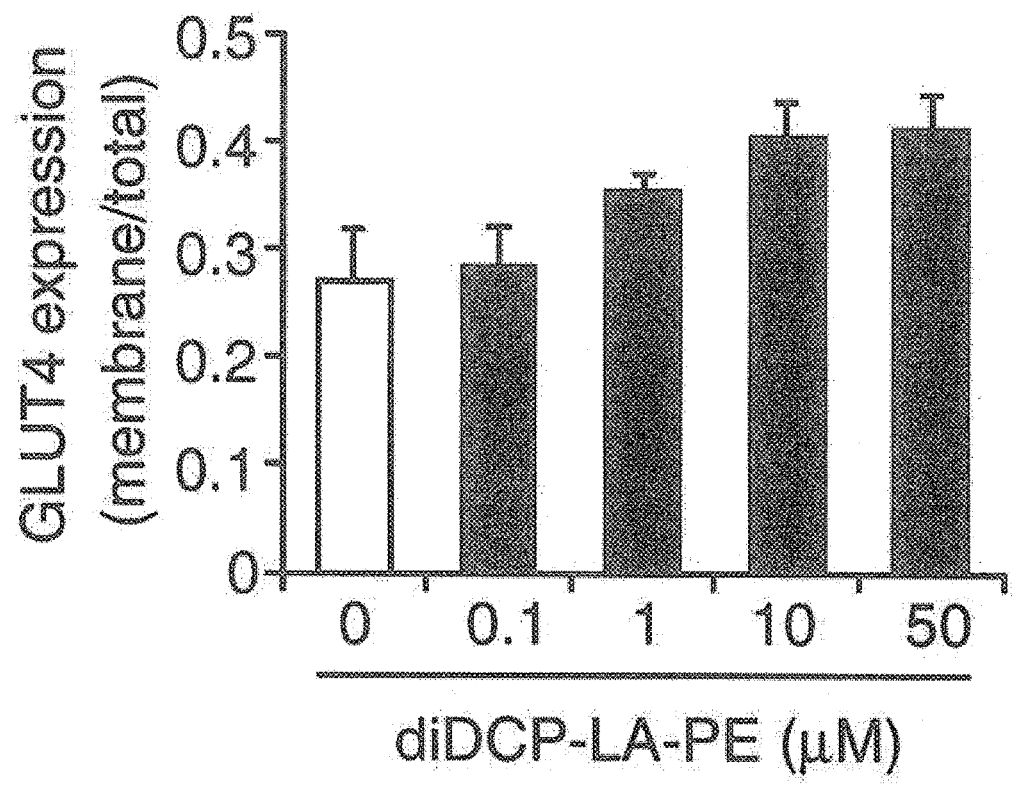
FIG. 8 is a graph showing a concentration-dependent effect of diDCP-LA-PE on cellular membrane transport of GLUT4 in 3T3L1-GLUT4 myc adipocytes. Without treatment with a given concentration of diDCP-LA-PE, or 20 min after the treatment, the cells were lysed and divided into cytoplasm fraction and cellular membrane fraction, and Western blotting was performed using an anti-c-myc antibody. In the graph, each column shows mean (±SD) ratio of signal intensity of GLUT4 in cellular membrane fraction/ signal intensity of GLUT4 in the whole cellular membrane fraction and cytoplasm fraction (n=4 in each experiment).
Figure 9:
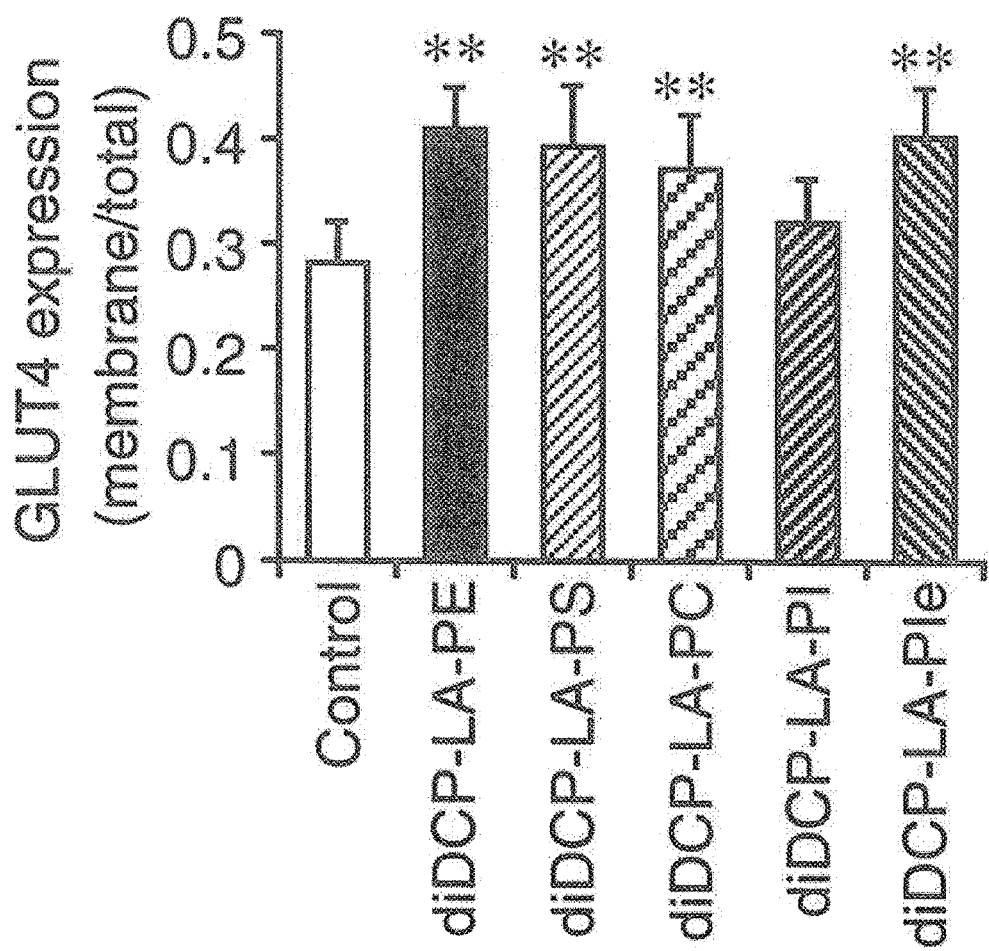
FIG. 9 is a graph showing that a phospholipid derivative promotes cellular membrane transport of GLUT4 in differentiated 3T3L1-GLUT4 myc adipocytes. Without treatment with various phospholipid derivatives (control), or 20 min after the treatment with 1 μM, the cells were lysed and divided into cytoplasm fraction and cellular membrane fraction, and Western blotting was performed using an anti-c-myc antibody. In the graph, each column shows mean (±SD) ratio of signal intensity of GLUT4 in cellular membrane fraction/signal intensity of GLUT4 in the whole cellular membrane fraction and cytoplasm fraction (n=4 in each experiment). *$P<0.05$, **$P<0.001$; value as compared to the control, unpaired t-test.diDCP-LA-PIe, diDCP-LA-PI enantiomers

The results are shown in FIGS. 7-9. From FIG. 7, it is clear that diDCP-LA-PE has, like insulin, an action to promote cellular membrane transport of GLUT4. From FIG. 8, it is clear that diDCP-LA-PE promotes cellular membrane transport of GLUT4 in a concentration-dependent manner. FIG. 9 shows that all phospholipid derivatives except natural type diDCP-LA-PI have an action to promote cellular membrane transport of GLUT4.

Experimental Example 5

Non-Insulin-Dependent Hypoglycemic Action (Material and Method)
Glucose Tolerance Test C57BL/KsJ-lepr$^{db}$/lepr$^{db}$ mouse (female, 8-week-old) (CLEA Japan; Tokyo, Japan) was used. The glucose tolerance test was performed using the mouse starved for 12 hr. Glucose (2 g/ml/kg body weight) was administered by gavage, and the time point thereof was taken as 0 h. diDCP-LA-PE (0.01, 0.1, 1, 3 mg/kg), insulin (0.75 U/kg) or brine was orally administered 30 min before administration of glucose. The blood (10 µl) was collected from the tail vein at the time points of 0, 30, 60, and 90 min, and each plasma sample which was labeled with p-aminobenzylethylester and prepared from the obtained blood was loaded on high performance liquid chromatography (HPLC) system (LC-10ATvp; Shimadzu Co., Kyoto, Japan). The glucose concentration was calculated from a peak area/concentration analytical curve prepared using the standard glucose solution.

(Results)

Figure 10:
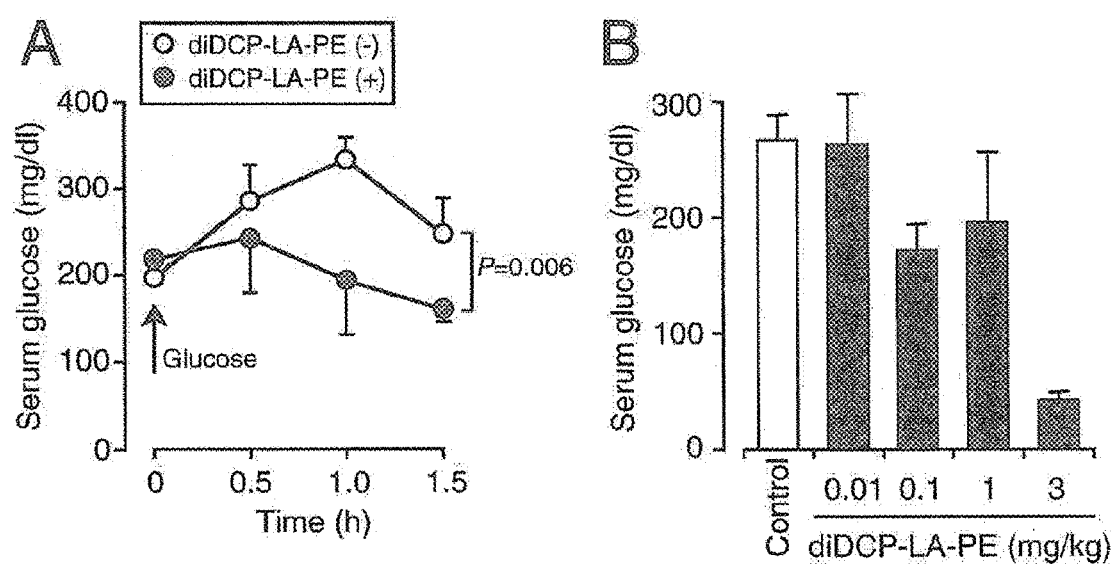
FIG. 10 is a graph showing lowered serum glucose level of C57BL/KsJ-lepr$^{db}$/lepr$^{db}$ mouse. (A) Mouse was placed in glucose starvation for 12 hr, glucose (2 g/kg) was orally administered (arrow), blood was recovered at a predetermined time and serum glucose assay was performed. Brine [diDCP-LA-PE(−)] or diDCP-LA-PE (1 mg/kg≈1 μM) [diDCP-LA-PE(+)] was orally administered 30 min before glucose administration. In the graph, each point shows mean (±SEM) glucose concentration (n=5 in each experiment). P value, Fisher's PLSD (Protected Least Significant Difference test) (B) Mouse was placed in glucose starvation for 12 hr, and brine (control) or diDCP-LA-PE was orally administered at a given concentration 30 min before oral administration of glucose. In the graph, each column shows mean (±SEM) serum glucose concentration 1 hr after glucose administration (n=5 in each experiment).

The results are shown in FIG. 10. The results show that diDCP-LA-PE has an action to decrease the blood glucose level in a dose-dependent manner on type 2 diabetes model mouse. This fact suggests a possibility that oral administration of diDCP-LA-PE may be a therapeutic drug for type 2 diabetes without requiring insulin.

Experimental Example 6

Effect on Type 1 Diabetes Model Mouse Using Streptozotocin (Material and Method)

C57BL/6J mouse (male, 8-week-old) (Japan SLC Inc.; Shizuoka, Japan) was used. Streptozotocin (STZ; 250 mg/kg) or saline as a control was injected intraperitoneally. After 4 days from the injection, an oral glucose tolerance test (OGTT) was performed.

(Results)

Figure 11:
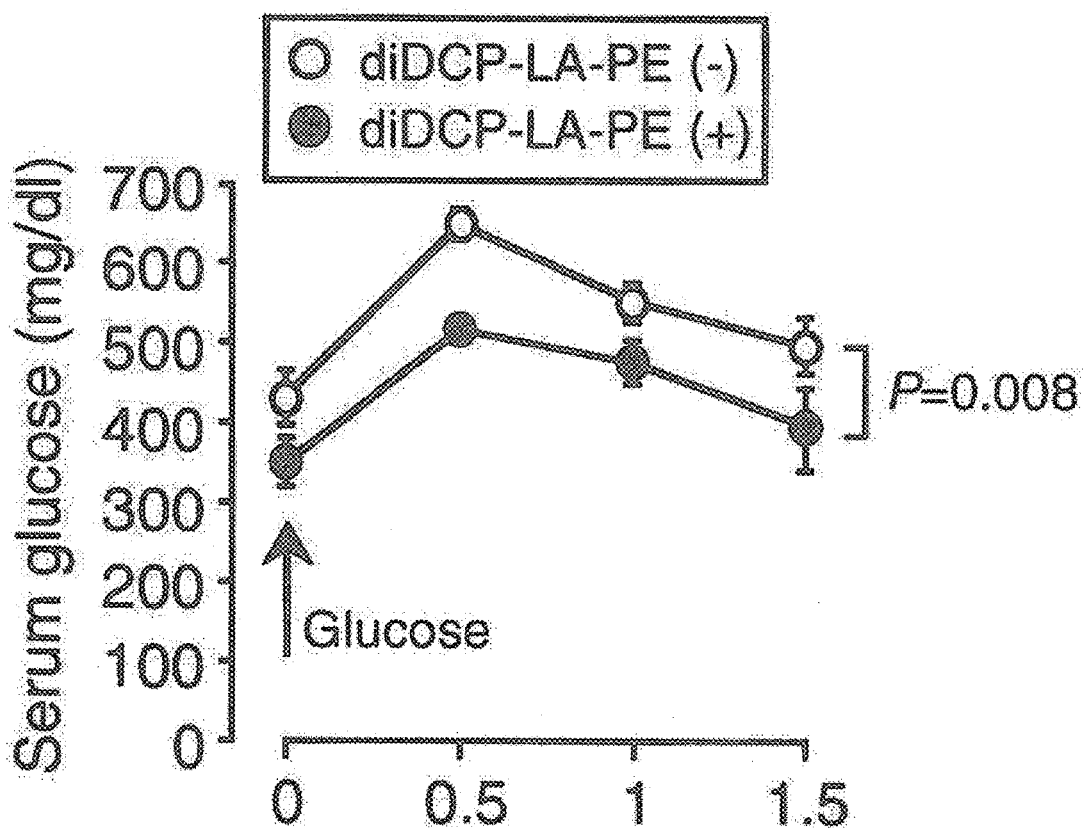
FIG. 11 is a graph showing that diDCP-LA-PE decreases the serum glucose level in streptozotocin (STZ)-treated mouse. Mouse was placed in glucose starvation for 12 hr, glucose (2 g/kg) was orally administered (arrow), blood was recovered at a predetermined time and serum glucose assay was performed. Brine [diDCP-LA-PE(−)] or diDCP-LA-PE (1 mg/kg≈1 μM)[diDCP-LA-PE(+)] was orally administered for 4 consecutive days before OGTT and 30 min before glucose administration. In the graph, each point shows mean (±SEM) glucose concentration (n=5 in each experiment). P value, Fisher's PLSD (Protected Least Significant Difference test)

The results are shown in FIG. 11. The results show that diDCP-LA-PE significantly suppresses an increase in the blood glucose of STZ treatment mouse. That is, diDCP-LA-PE is shown to be also effective for type 1 diabetes.

Experimental Example 7

Promoting Action on Transfer of Sugar Transport Carrier GLUT4 to Cellular Membrane-2

(Material and Method)

The experiment was performed in the same manner as in Experimental Example 4 except that 3T3L1-GLUT4myc adipocytes having a knocked-down insulin receptor were used and incubation with diDCP-LA-EA was performed in the absence of insulin.

(Results)

Figure 12:
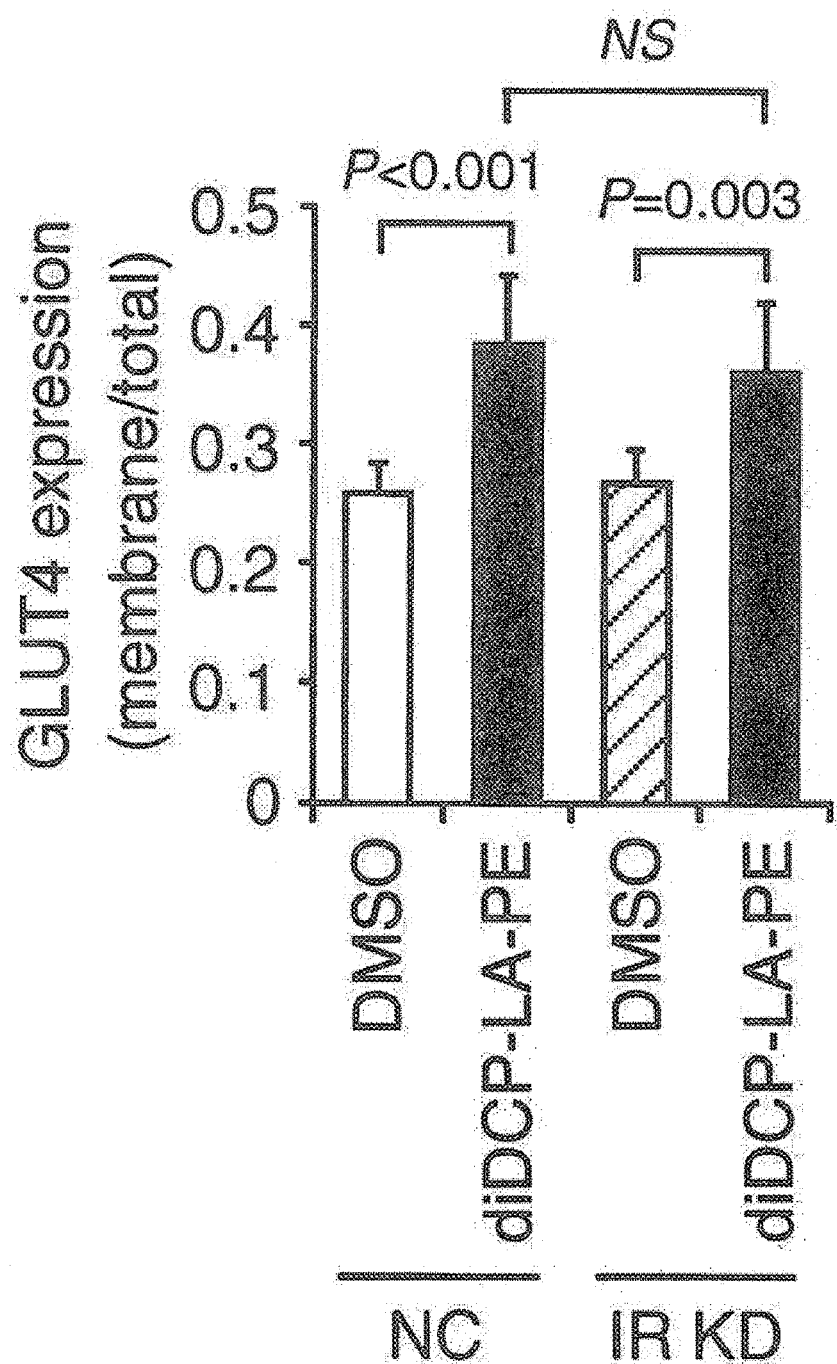
FIG. 12 is a graph showing that diDCP-LA-PE promotes cellular membrane transport of GLUT4 in differentiated 3T3L1-GLUT4 myc adipocytes wherein insulin receptor has been knocked-down. The cells were transfected with NC siRNA(NC) as a negative control or insulin receptor siRNA (IR KD) and, 48 hr later, without treatment with diDCP-LA-PE or 20 min after the treatment with 1 μM, the cells were lysed and divided into cytoplasm fraction and cellular membrane fraction, and Western blotting was performed using an anti-c-myc antibody. In the graph, each column shows mean (±SD) ratio of signal intensity of GLUT4 in cellular membrane fraction/signal intensity of GLUT4 in the whole cellular membrane fraction and cytoplasm fraction (n=4 in each experiment). P value, Dunnett's test. NS; not significant

The results are shown in FIG. 12. From FIG. 12, it is clear that diDCP-LA-PE can promote transfer of GLUT4 to a cellular membrane in an insulin receptor independent manner. That is, it shows that diDCP-LA-PE can substitute for an intracellular insulin receptor signal (decreasing blood glucose level in an insulin/insulin receptor independent manner) even in the absence of insulin. From the results, it is clear that diDCP-LA-PE is also effective for the treatment of type 1 diabetes which is considered to essentially require insulin for the treatment.

INDUSTRIAL APPLICABILITY

A phospholipid compound containing an unsaturated fatty acid derivative having a cyclopropane ring, which is provided by the present invention, has pharmacological actions (protein tyrosine phosphatase 1B (PTP1B) inhibitory action, Akt activating action, protein phosphorylated enzyme C (PKC) activating action, PKCι and PKCζ activating action, promoting action on transfer of glucose transporter 4 (GLUT4) to cellular membrane and non-insulin-dependent blood glucose level lowering action) superior in the improvement of cognitive function and/or treatment of diabetes, and therefore, is useful as a therapeutic drug for dementia or a therapeutic drug for diabetes. It is also useful as various reagents based on such pharmacological actions.

This application is based on a patent application No. 2013-027992 filed in Japan (filing date: Feb. 15, 2013), the contents of which are incorporated in full herein.

The invention claimed is:

1. A medicine comprising a phospholipid compound containing an unsaturated fatty acid having a cyclopropane ring as an active ingredient, wherein the phospholipid compound is 1,2-o-bis-[8-{2-(2-pentyl-cyclopropylmethyl)-cyclopropyl}-octanoyl]-sn-glycero-3-phosphatidylethanolamine(diDCP-LA-PE).

2. The medicine according to claim 1, which is a therapeutic drug for diabetes.

3. The medicine according to claim 2, wherein the diabetes is type 1 diabetes or type 2 diabetes.

4. The medicine according to claim 1, which is a therapeutic drug for dementia.

5. The medicine according to claim 4, wherein the dementia is Alzheimer-type dementia.

6. The medicine according to claim 1, which is an anti-aging drug.

7. A reagent comprising a phospholipid compound containing an unsaturated fatty acid derivative having a cyclopropane ring as an active ingredient, wherein the phospholipid compound is 1,2-o-bis-[8-{2-(2-pentyl-cyclopropylmethyl)-cyclopropyl}-octanoyl]-sn-glycero-3-phosphatidylethanolamine(diDCP-LA-PE).

8. The reagent according to claim 7, which is a protein tyrosine phosphatase 1B inhibitor.

9. The reagent according to claim 7, which is an Akt activator.

10. The reagent according to claim 7, which is a protein phosphorylated enzyme C (PKC) activator.

11. The reagent according to claim 10, wherein the PKC is PKCι and/or PKCζ.

12. A compound that is
1,2-o-bis-[8-{2-(2-pentyl-cyclopropylmethyl)-cyclopropyl}-octanoyl]-sn-glycero-3-phosphatidylethanolamine (diDCP-LA-PE).

* * * * *